(12) United States Patent
Voss et al.

(10) Patent No.: US 11,089,985 B2
(45) Date of Patent: *Aug. 17, 2021

(54) SYSTEMS AND METHODS FOR USING MOBILE AND WEARABLE VIDEO CAPTURE AND FEEDBACK PLAT-FORMS FOR THERAPY OF MENTAL DISORDERS

(71) Applicants: The Board of Trustees of the Leland Stanford Junior University, Stanford, CA (US); Catalin Voss, Stanford, CA (US)

(72) Inventors: Catalin Voss, Stanford, CA (US); Nicholas Joseph Haber, Palo Alto, CA (US); Dennis Paul Wall, Palo Alto, CA (US); Aaron Scott Kline, Saratoga, CA (US); Terry Allen Winograd, Stanford, CA (US)

(73) Assignees: The Board of Trustees of the Leland Stanford Junior University, Stanford, CA (US); Catalin Voss, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/066,979

(22) Filed: Oct. 9, 2020

(65) Prior Publication Data
US 2021/0022657 A1    Jan. 28, 2021

Related U.S. Application Data

(63) Continuation of application No. 15/589,877, filed on May 8, 2017, now Pat. No. 10,835,167.
(Continued)

(51) Int. Cl.
*A61B 5/16*      (2006.01)
*A61B 5/1171*    (2016.01)
(Continued)

(52) U.S. Cl.
CPC ............ *A61B 5/165* (2013.01); *A61B 5/0002* (2013.01); *A61B 5/0036* (2018.08);
(Continued)

(58) Field of Classification Search
CPC ..... A61B 5/165; A61B 5/0036; A61B 5/0205; A61B 5/6803; A61B 5/4836;
(Continued)

(56) References Cited

U.S. PATENT DOCUMENTS 8,140,014 B2   3/2012  Liao
9,019,174 B2   4/2015  Jerauld
(Continued)

FOREIGN PATENT DOCUMENTS

CN   105536118 A   5/2016
CN   109475294 A   3/2019
(Continued)

OTHER PUBLICATIONS

Extended European Search Report for European Application No. 17810680.3, Search completed Dec. 4, 2019, dated Dec. 11, 2019, 9 Pgs.
(Continued)

*Primary Examiner* — John B Strege
(74) *Attorney, Agent, or Firm* — KPPB LLP

(57) ABSTRACT

Behavioral and mental health therapy systems in accordance with several embodiments of the invention include a wearable camera and/or a variety of sensors (accelerometer, microphone, among various other) connected to a computing system including a display, audio output, holographic output, and/or vibrotactile output to automatically recognize social cues from images captured by at least one camera and provide this information to the wearer via one or more outputs such as (but not limited to) displaying an image,
(Continued)

displaying a holographic overlay, generating an audible signal, and/or generating a vibration.

19 Claims, 21 Drawing Sheets

Related U.S. Application Data

(60) Provisional application No. 62/333,108, filed on May 6, 2016.

(51) Int. Cl.
| | |
|---|---|
| *A61B 5/00* | (2006.01) |
| *A61B 5/0205* | (2006.01) |
| *G16H 50/30* | (2018.01) |
| *G16H 50/20* | (2018.01) |
| *G16H 40/63* | (2018.01) |
| *G16H 30/40* | (2018.01) |
| *G16H 20/70* | (2018.01) |
| *A61B 5/11* | (2006.01) |

(52) U.S. Cl.
CPC .......... *A61B 5/0205* (2013.01); *A61B 5/1176* (2013.01); *A61B 5/4836* (2013.01); *A61B 5/681* (2013.01); *A61B 5/6803* (2013.01); *G16H 20/70* (2018.01); *G16H 30/40* (2018.01); *G16H 40/63* (2018.01); *G16H 50/20* (2018.01); *G16H 50/30* (2018.01); *A61B 5/1114* (2013.01); *A61B 5/1126* (2013.01); *A61B 5/1128* (2013.01); *A61B 5/742* (2013.01); *A61B 5/7405* (2013.01); *A61B 5/7455* (2013.01)

(58) Field of Classification Search
CPC ..... A61B 5/1176; A61B 5/681; A61B 5/0002; A61B 5/1126; A61B 5/1128; A61B 5/1114; A61B 5/7405; A61B 5/7455; A61B 5/742; A61B 5/163; G16H 50/30; G16H 50/20; G16H 50/00; G16H 40/63; G16H 30/40; G16H 20/70; G06K 9/00302
See application file for complete search history.

(56) References Cited

U.S. PATENT DOCUMENTS

| | | | | |
|---|---|---|---|---|
| 9,111,134 | B1* | 8/2015 | Rogers | G06K 9/00315 |
| 10,835,167 | B2* | 11/2020 | Voss | A61B 5/0036 |
| 2002/0028021 | A1 | 3/2002 | Foote et al. | |
| 2005/0102246 | A1* | 5/2005 | Movellan | G06N 3/004 706/12 |
| 2007/0258645 | A1 | 11/2007 | Gokturk et al. | |
| 2008/0177197 | A1 | 7/2008 | Lee et al. | |
| 2011/0251493 | A1 | 10/2011 | Poh et al. | |
| 2013/0187835 | A1 | 7/2013 | Vaught et al. | |
| 2014/0063236 | A1 | 3/2014 | Shreve et al. | |
| 2014/0315168 | A1 | 10/2014 | Movellan et al. | |
| 2014/0375820 | A1 | 12/2014 | Priyantha et al. | |
| 2015/0079560 | A1 | 3/2015 | Cowan | |
| 2015/0099946 | A1 | 4/2015 | Sahin | |
| 2015/0131850 | A1 | 5/2015 | Qvarfordt | |
| 2019/0015033 | A1* | 1/2019 | Sahin | G16H 50/20 |

FOREIGN PATENT DOCUMENTS

| | | |
|---|---|---|
| EP | 3452935 A1 | 3/2019 |
| WO | 2014127333 A1 | 8/2014 |
| WO | 2015023952 A1 | 2/2015 |
| WO | 2016035268 A1 | 3/2016 |
| WO | 2017213780 A1 | 12/2017 |

OTHER PUBLICATIONS

International Preliminary Report on Patentability for International Application PCT/US2017/031616, dated Nov. 6, 2018, dated Nov. 15, 2018, 8 Pgs.
Bosseler et al., "Development and Evaluation of a Computer-Animated Tutor for Vocabulary and Language Learning in Children with Autism", Journal of Autism and Developmental Disorders, vol. 33, No. 6, Dec. 2003, pp. 653-672.
Hetzroni et al., "Effects of a Computer-Based Intervention Program on the Communicative Functions of Children with Autism", Journal of Autism and Developmental Disorders, vol. 34, No. 2, Apr. 2004, pp. 95-113.
Jones et al., "Attention to eyes is present but in decline in 2-6-month-old infants later diagnosed with autism", Nature, vol. 504, Nov. 6, 2013, pp. 427-431.
Lerman et al., "A Rapid Assessment of Skills in Young Children with Autism", Journal of Applied Behavior Analysis, vol. 37, No. 1, Spring 2004, pp. 11-26.
Lobue et al., "The Child Affective Facial Expression (CAFE) set: validity and reliability from untrained adults", Frontiers in Psychology, vol. 5, No. 1532, Jan. 2015, 8 pgs.
Lucey et al., "The Extended Cohn-Kanade Dataset (CK+): A complete dataset for action unit and emotion-specified expression", Proceedings of the IEEE Computer Society Conference on Computer Vision and Pattern Recognition—Workshops, San Francisco, California, Jun. 13-18, 2010, pp. 94-101, DOI: 10.1109/CVPRW.2010.5543262.
Madsen et al., "Technology for Just-In-Time In-Situ Learning of Facial Affect for Persons Diagnosed with an Autism Spectrum Disorder", Proceedings of the 10th international ACM SIGACCESS conference on Computers and accessibility, Halifax, Nova Scotia, Canada, Oct. 13-15, 2008, 7 pgs.
Myles et al., "Sensory Issues in Children with Asperger Syndrome and Autism", Education and Training in Developmental Disabilities, vol. 39, No. 4, 2004, pp. 283-290.
Sasson et al., "Eye Tracking Young Children with Autism", Journal of Visualized Experiments, vol. 61, e3675, Mar. 2012, 6 pgs.
Silver et al., "Evaluation of a New Computer Intervention to Teach People with Autism or Asperger Syndrome to Recognize and Predict Emotions in Others", Autism, vol. 5, No. 3, Sep. 1, 2001, pp. 299-316.
Valdez et al., "Effects of Color on Emotions", Journal of Experimental Psychology: General, vol. 123, No. 4, 1994, pp. 394-409.
Wingate et al., "Prevalence of Autism Spectrum Disorder Among Children Aged 8 Years—Autism and Developmental Disabilities Monitoring Network, 11 Sites, United States, 2010", Morbidity and Mortality Weekly Report (MMWR) Surveillance Summaries, vol. 63, No. 2, Mar. 28, 2014, 24 pgs.
International Search Report and Written Opinion for International Application No. PCT/US2017/031616, Search completed Aug. 22, 2017, dated Sep. 25, 2017, 18 Pgs.
"Pupil Labs—Home Page", Pupil Labs, Mar. 18, 2016, retrieved from https://web.archive.org/web/20160318050614/https://pupil-labs.com/pupil/ on Aug. 8, 2017, 4 pages.
Bodor et al., "Vision-based human tracking and activity recognition", Proc. of the 11th Mediterranean Conf. on Control and Automation, Jun. 2003, pp. 18-20.
Bruna et al., "Invariant Scattering Convolution Networks", arXiv:1203.1513v2 [cs.CV], Mar. 8, 2012, pp. 1-15.
Cho et al., "On the Properties of Neural Machine Translation: Encoder-Decoder Approaches", arXiv:1409.1259v2 [cs.CL], Oct. 7, 2014, pp. 1-9.
Choy et al., "3D-R2N2: A Unified Approach for Single and Multi-view 3D Object Reconstruction", arXiv:1604.00449v1 [cs.CV], Apr. 2, 2016, 17 pages.
Culotta et al., "Corrective feedback and persistent learning for information extraction", Artificial Intelligence, vol. 170, Issues 14-15, Oct. 2006, pp. 1101-1122.
Dantone et al., "Human Pose Estimation Using Body Parts Dependent Joint Regressors", 2013 IEEE Conference on Computer Vision and Pattern Recognition, Jun. 23-28, 2013, Portland, OR, USA, pp. 3041-3048.

(56) References Cited

OTHER PUBLICATIONS

De La Torre et al., "Facial Expression Analysis", Visual Analysis of Humans, Springer-Verlag London Limited, 2011, pp. 377-409, https://doi.org/10.1007/978-0-85729-997-0_19.

El Kaliouby et al., "Mind reading machines: automated inference of cognitive mental states from video", 2004 IEEE International Conference on Systems, Man and Cybernetics (IEEE Cat. No. 04CH37583), vol. 1, Oct. 10-13, 2004, The Hague, Netherlands, pp. 682-688.

Fiaz et al., "Vision based human activity tracking using artificial neural networks", 2010 International Conference on Intelligent and Advanced Systems, Jun. 15-17, 2010, Kuala Lumpur, Malaysia, pp. 1-5.

Haber et al., "A practical approach to real-time neutral feature subtraction for facial expression recognition", 2016 IEEE Winter Conference on Applications of Computer Vision (WACV), Mar. 7-10, 2016, pp. 1-9.

Hernandez et al., "BioGlass: Physiological parameter estimation using a head-mounted wearable device", 2014 4th International Conference on Wireless Mobile Communication and Healthcare—Transforming Healthcare Through Innovations in Mobile and Wireless Technologies (MOBIHEALTH), Nov. 3-5, 2014, Athens, Greece, pp. 55-58.

Hochreiter et al., "Long Short-Term Memory", Neural Computation, vol. 9, Issue 8, Nov. 15, 1997, pp. 1735-1780.

Krizhevsky et al., "ImageNet Classification with Deep Convolutional Neural Networks", Advances in Neural Information Processing Systems (NIPS 2012), vol. 25, 2012, pp. 1-9.

Mao et al., "Cross-Domain Facial Expression Recognition Using Supervised Kernel Mean Matching", 2012 11th International Conference on Machine Learning and Applications, Dec. 12-15, 2012, Boca Raton, FL, USA, pp. 326-332.

Settles, Burr, "Active Learning", Synthesis Lectures on Artificial Intelligence and Machine Learning, Morgan Claypool Publishers, 2012, 116 pages.

Szegedy et al., "Going deeper with convolutions", 2015 IEEE Conference on Computer Vision and Pattern Recognition (CVPR), Jun. 7-12, 2015, pp. 1-9.

Tan et al., "Enhanced Local Texture Feature Sets for Face Recognition Under Difficult Lighting Conditions", IEEE Transactions on Image Processing, vol. 19, Issue 6, Jun. 2010, pp. 1635-1650.

Timm et al., "Accurate Eye Centre Localisation by Means of Gradients", VISAPP 2011—Proceedings of the Sixth International Conference on Computer Vision Theory and Applications, Mar. 5-7, 2011, Vilamoura, Algarve, Portugal, pp. 1-6.

Walecki et al., "Variable-state latent conditional random fields for facial expression recognition and action unit detection", 2015 11th IEEE International Conference and Workshops on Automatic Face and Gesture Recognition (FG), May 4-8, 2015, Ljubljana, Slovenia, pp. 1-8.

Wang et al., "Early Facial Expression Recognition Using Hidden Markov Models", 2014 22nd International Conference on Pattern Recognition, Aug. 24-28, 2014, Stockholm, Sweden, pp. 4594-4599.

Wqllmer et al., "Analyzing the memory of BLSTM Neural Networks for Enhanced Emotion Classification in Dyadic Spoken Interactions", 2012 IEEE International Conference on Acoustics, Speech and Signal Processing (ICASSP), Mar. 25-30, 2012, Kyoto, Japan, pp. 4157-4160.

* cited by examiner

FIG. 19

| SRS Subsection | Mean | | Mean Difference | SD | | SEM | |
|---|---|---|---|---|---|---|---|
| | Intake | Conclusion | | Intake | Conclusion | Intake | Conclusion |
| SRS Total | 80.07 | 72.93 | -7.143*** | 9.531 | 10.292 | 2.547 | 2.751 |
| SRS Social Awareness | 78.07 | 71.21 | -6.857*** | 11.194 | 11.544 | 2.992 | 3.085 |
| SRS Social Cognition | 74.86 | 69.93 | -4.929* | 8.160 | 10.594 | 2.181 | 2.831 |
| SRS Communication | 78.93 | 72.57 | -6.36*** | 10.477 | 10.308 | 2.8000 | 2.755 |
| SRS Social Motivation | 68.71 | 64.79 | -3.929* | 9.523 | 9.784 | 2.545 | 2.615 |
| SRS Autistic Mannerisms | 83.07 | 72.07 | -11.000** | 18.036 | 11.737 | 4.820 | 3.137 |

Table 3. Descriptive statistics and main effects from a repeated measures ANOVA analysis. *p<.05, p<.01, *p<.001

*FIG. 20*

Change in SRS Scores from Intake to Conclusion by SRS subscale.

SYSTEMS AND METHODS FOR USING MOBILE AND WEARABLE VIDEO CAPTURE AND FEEDBACK PLAT-FORMS FOR THERAPY OF MENTAL DISORDERS

CROSS REFERENCE TO RELATED APPLICATIONS

This application is a continuation of U.S. patent application Ser. No. 15/589,877, entitled "Systems and Methods for Using Mobile and Wearable Video Capture and Feedback Plat-Forms for Therapy of Mental Disorders" to Voss et al., filed on May 8, 2017, which claims the benefit of U.S. Provisional Patent Application No. 62/333,108, entitled "Systems and Methods for Using Mobile and Wearable Video Capture and Feedback Systems as Therapy for Mental Disorders" to Voss et al., filed on May 6, 2016, the disclosures of which are hereby incorporated by reference in their entirety.

STATEMENT REGARDING FEDERALLY SPONSORED RESEARCH OR DEVELOPMENT

This invention was made with Government support under contract EB025025 awarded by the National Institutes of Health. The Government has certain rights in the invention.

FIELD OF THE INVENTION

The present invention is related to providing systems and methods for using mobile and wearable video capture systems to provide therapy for behavioral disorders. In particular, the computing system runs a software system that utilizes classifiers to detect expressions in faces visible within images captured by the system and provides feedback to a user as part of their therapeutic treatment.

BACKGROUND

Mental disorders like autism, anxiety, depression, bipolar disorders, schizophrenia, traumatic brain injury, Alzheimer's, and Parkinson's disease are known to negatively affect social interactions. For example, approximately one in 68 children and one in 46 boys has autism and struggles to recognize facial expressions, make eye contact, and engage in social interactions due to their condition.

Gaining or regaining such social skills can require intensive behavioral intervention that is often expensive, difficult to access, and inconsistently administered. The current standard of care for autism and some other disorders, for example, involves "flashcard therapy" involving painstaking memorization of facial emotions. As a result, many children with autism fail to build core social skills and can quickly regress down a path of isolation that worsens their symptoms.

SUMMARY OF THE INVENTION

Systems and methods for using mobile and wearable video capture systems to provide therapy for behavioral and mental health disorders in accordance with various embodiments of the invention are disclosed. In one embodiment, an image processing system, includes: at least one camera for capturing images of a surrounding environment; at least one processor and memory containing software; and the software directs the at least one processor to: obtain data that includes a sequence of images captured by the at least one camera; detect a face for at least one person within several images in the sequence of images; perform neutral feature estimation and subtraction on the detected face of the at least one person in each of the several images and using a classifier to detect at least one emotional cue in the face based upon the several images; identify at least one emotion based on the emotional cue; and display at least one emotion indicator label in real time to provide therapeutic feedback.

In a further embodiment, the system includes a wearable video capture system that includes at least one outward facing camera.

In yet a further embodiment, the wearable video capture system is selected from the group: a virtual reality headset, a mixed-reality headset, an augmented reality headset, and glasses that include a heads-up display.

In another embodiment, the wearable video capture system communicates with at least one mobile device, and the at least one processor is executing on the at least one mobile device.

In a still further embodiment, the software directs the at least one processor to obtain supplementary data that includes data captured from at least one sensor selected from the group: a microphone, an accelerometer, a gyroscope, an eye tracking sensor, a head-tracking sensor, a body temperature sensor, a heart rate sensor, a blood pressure sensor, and a skin conductivity sensor.

In still another embodiment, the software directs the at least one processor to display at least one emotion indicator label in real time to provide therapeutic feedback by performing at least one of displaying a label within a heads-up display, generating an audible signal, generating a vibration, displaying a holographic overlay, and displaying an image.

In yet another embodiment, the software directs the at least one processor to process image data at a higher resolution within a region of interest related to a detected face within an image.

In still another embodiment again, the region of interest is a bounding region around the detected face, where processing the data also uses a moving average filter to smoothen the bounding region of interest.

In a yet further embodiment again, the software directs the at least one processor to perform neutral feature estimation and subtraction on the at least one person by: performing face detection; performing fiducial point face tracking; performing registration of the face to a canonical size and pose; performing lighting normalization preprocessing; generating a Histogram of Gradients feature extraction in a region of interest about the face; and performing classification of the face's expression via a logistic regression classifier; and filtering of the resulting classification In yet another embodiment again, the expression cue includes information selected from the group consisting of facial expressions, facial muscle movements, body language, gestures, body pose, eye contact events, head pose, features of a conversation, fidgeting, and anxiety information.

In a yet further embodiment again, the classifier is trained using a training data set of statistically representative social expression data and that provides event-based social cues.

In still another additional embodiment, the software directs the at least one processor to supplement the training set with user-labeled data of target individuals.

In a still further embodiment again, the software directs the at least one processor to train the classifier using the training data and the user-labeled data of target individuals so that the classifier achieves higher performance detecting at least one emotional cue in the face of the target individuals compared with the performance of the classifier detecting at least one emotional cue in the face of other individuals in the training data.

In another embodiment again, the software directs the at least one processor to: prompt a user to label data for a target individual with at least one emotional cue label; and store the user-labeled data for the target individual in memory.

In still yet another embodiment again, the software direct the at least one processor to store social interaction data and provide a user interface for review of the social interaction data.

In a still yet further additional embodiment, the classifier is a regression machine that provides continuous social cues.

In still yet another additional embodiment, the classifier is trained as visual time-dependent classifiers using video data of standard facial expressions and with expressive talking sequences.

In still yet another embodiment again, the software direct the at least one processor to detect gaze events using at least one inward-facing eye tracking data in conjunction with outward-facing video data.

In a yet further additional embodiment again, the software direct the at least one processor to provide a review of activities recorded and provide user behavioral data generated as a reaction to the recorded activities.

In still another further embodiment, performing neutral feature estimation and subtraction on the face of the at least one person includes performing neutral expression subtraction based upon outputs of a first expression classifier trained on neutral-subtracted features and a second 2-class neutral/expressive classifier trained on raw (not neutral-subtracted) features.

In one embodiment, a behavioral therapy system includes: at least one camera for capturing images of a surrounding environment; at least one processor and memory containing software; where the software directs the at least one processor to display, for each of several images previously stored within the memory of the system, an image of a face of person expressing a particular emotion, where the image is associated with the particular emotion; receive an input from a user viewing the image regarding an emotion that the user has selected as illustrating the emotion being portrayed by the face of the person; determine whether the received input from the user matches the particular emotion associated with the particular image; and provide feedback to the user based on their selections.

In another embodiment, a behavioral therapy system includes: at least one camera for capturing images of a surrounding environment; at least one processor and memory containing software; where the software directs the at least one processor to: capture video of a person in real-time; detect an emotion for a face of the person using at least one classifier; provide an indication regarding a different emotion that should be provoked in the person that is currently not being detected; determine whether the emotion has been elicited within a certain time period; and provide feedback to a user of the system regarding their ability to elicit the emotion.

BRIEF DESCRIPTION OF THE DRAWINGS

The description will be more fully understood with reference to the following figures and data graphs, which are presented as various embodiments of the disclosure and should not be construed as a complete recitation of the scope of the disclosure, wherein:

FIG. 19 illustrates an algorithm for neutral subtraction in accordance with an embodiment of the invention.

FIG. 20 illustrates results from a particular study showing SRS scores from intake to conclusion.

DETAILED DESCRIPTION

Figure 1:
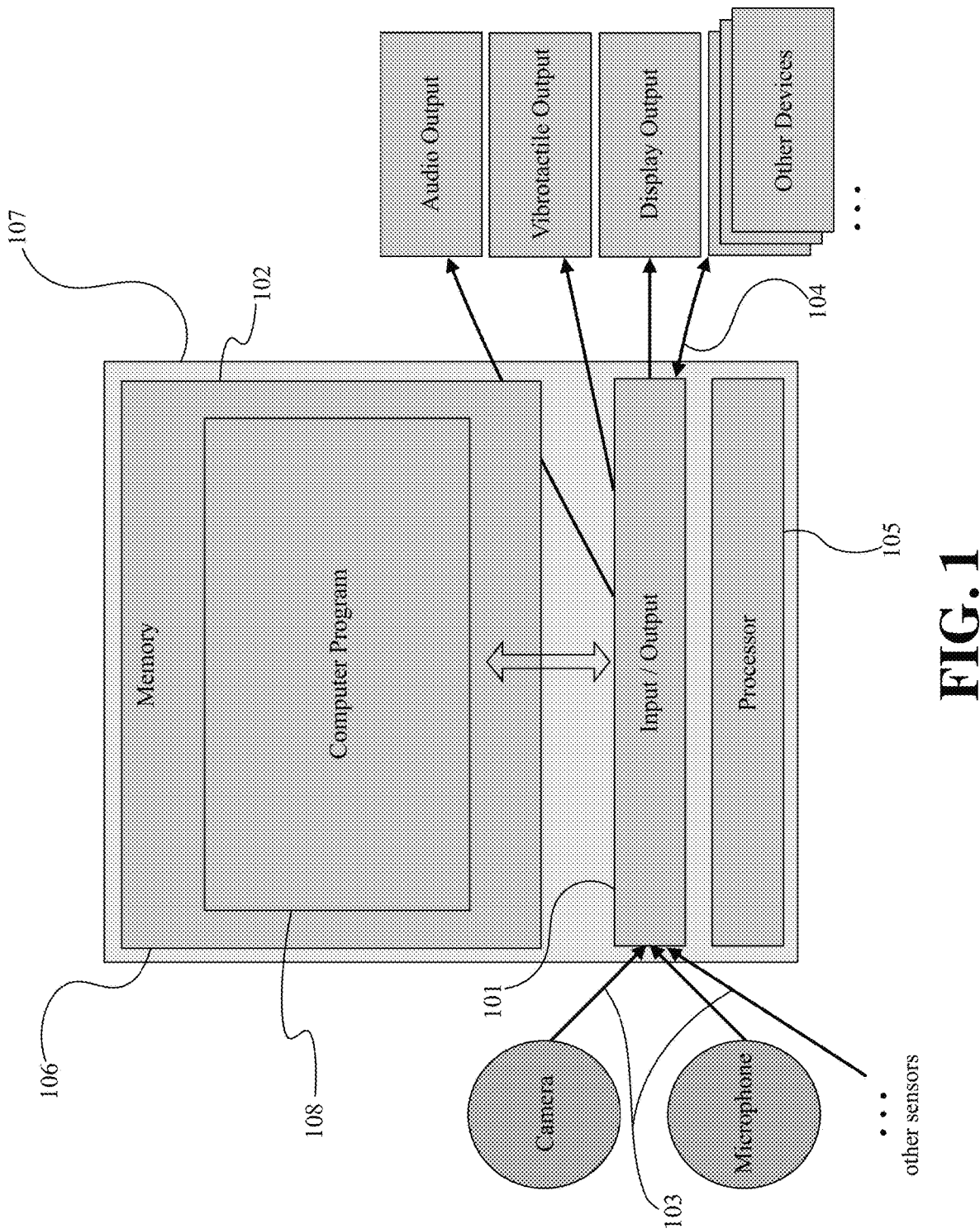
FIG. 1 illustrates a behavioral therapy system in accordance with an embodiment of the invention.

Turning now to the drawings, systems and methods for using mobile and wearable video capture systems to provide therapy for behavioral and mental health disorders in accordance with various embodiments of the invention are illustrated. The arrival of mobile and wearable devices (such as smart glasses like Google Glass and devices that include mixed reality displays similar to the Microsoft Hololens) presents the opportunity to develop applications that take the social learning experience into the home of patients, for example by giving minimally obtrusive social cues in real time on a wearable system, by reviewing certain observable and measurable behavioral progress indicators such as (but not limited to) amount and type of eye contact, or by reviewing video recordings of emotional interaction to identify what went well or poorly in a given situation. In the following detailed description, systems for using mobile and wearable video capture approaches as therapy of behavioral disorders as well as various novel methods that enable this system and may be useful in other similar arenas of medical or nonmedical social recognition tasks are disclosed.

Behavioral therapy systems in accordance with several embodiments of the invention include a wearable camera and/or a variety of sensors (accelerometer, microphone, among various other) connected to a computing system including a display, audio output, holographic output, and/or vibrotactile output to automatically recognize social cues from images captured by at least one camera and provide this information to the wearer via one or more outputs such as (but not limited to) displaying an image, displaying a holographic overlay, generating an audible signal, and/or generating a vibration. In a number of embodiments, the wearable behavioral therapy system takes the form of an augmented reality, mixed reality, or virtual reality headset that incorporates a camera and relies upon processors within the headset and/or a processor(s) in a mobile phone handset in communication with the headset via a wired and/or wireless data connection to process image data and generate displays. In certain embodiments, the subject (an individual with a mental disorder) wears the headset that captures video frames through an outward-facing camera along with other physiological (e.g. body temperature, heart rate) and behavioral/sensory data (e.g. audio signals, eye tracking, head-tracking, etc.) and sends these data to an application running on a mobile phone in real time. In several embodiments, a computing system runs a software system that utilizes classifiers to detect faces and/or expressive events in faces visible within images captured by the camera. In a number of embodiments, the computing system is also able to identify other social cues from captured image and/or other sensor data. In certain embodiments, a machine learning system is utilized to train one or more classifiers based upon a training data set of statistically representative social expression data. The computing system can utilize the classifiers to identify and/or compute the likelihood of specific social cues (e.g. about emotions of people that the subject interacts with) and can convey the presence of detected faces and/or detected social cues to the wearer through audio and/or visual feedback. Further, the computing system can store the social interaction data locally or via a remote storage service and can provide a user interface for curated review of these data.

The following describes, in accordance with many embodiments of the invention, multiple modifications that may be made to the system and a number of methods used to enable various components of the system, calibration of the machine learning components of the system to work well for particular participants and their caregivers, actively training the system to improve performance on those people, extending the capabilities of the machine learning components, and integrating the proposed system into the context of common behavioral therapy.

At a high level, the wearable behavioral therapy system in many embodiments can perform a variety of functions including (but not limited to) any combination of the following:

1. During unstructured social interactions that are part of a patient's everyday life (e.g. dinner), the wearable device can be used as a real-time social interaction aid.

2. To provide more engaging modes of interaction, the system can include specific gamified activities that encourage behavioral reinforcement in a way that best takes advantage of the system and/or provides appropriate therapeutic value. One example of such an activity is a game in which a group of children is challenged to "capture" a certain number of selected emotions by provoking them in another person (e.g., an adult, sibling) who makes the face that contains the emotion, e.g., by making a compliment to provoke a happy face. Another example is to reward patients for mimicking expressions of others.

3. After periods of use, patients and their caregivers may review activities recorded from the patient's point of view (referring to other's interactions with each other and towards the patient) as well as patient reactions to those situations in the form of behavioral and physiological data (for example eye contact made, expressions mimicked, etc.)

4. Following use of the system, the resulting data may be supplemented with some user-directed labeling (e.g. in the application of expression recognition, a user could correct "incorrectly" classified sequences in a video). The (perhaps relabeled) data can then be used to improve the machine learning components of the system to either improve recognition accuracy for the given task or learn to recognize social interactive events beyond the given task.

Naturally, any combination of these features may be appropriate for users of differing conditions, ages, families, and so on.

The following will describe various system components that are utilized to enable these features in many embodiments of the invention and how they interact at a high level, then explain how one may implement features 1-4 specifically, and then describe some extensions of how the system could be architected differently while still going after similar therapeutic goals.

Behavioral Therapy Technology System

Returning to the drawings, FIG. 1 illustrates a behavioral therapy technology system in accordance with an embodiment of the invention that includes a computing device 107 that enables performance of data processing and user interface methods similar to those described herein. A computing device can for example be a smart phone, desktop computer, laptop, smart TV, smart watch, smart glasses, and other commonly described computers. The processor 105 of the computing device executes computer programs written in memory 106. The processor works in conjunction with the I/O device 101 to direct data to memory or remote storage and to send data from memory or remote storage to the processor for processing or to the communications network. The processor can be, for example, any commercially available processor, or plurality of processors, adapted for use in the user computer (e.g., Intel® Xeon® multicore processors, Intel® micro-architecture Nehalem, AMD Opteron™ multicore processors, etc.). As one skilled in the art will appreciate, the processor may also include components that allow the computing device to be connected to sensors such as a camera, as well as a display, keyboard, mouse, trackball, trackpad and/or any other user input/output device (not shown) or to view content (e.g., a graphics or video card).

The memory may store the computer instructions of the instant invention and data (e.g., raw data, analyzed data, video content, etc.). As such, the memory may include both non-volatile memory such as hard disks, flash memory, optical disks, and the like, and volatile memory such as SRAM, DRAM, SDRAM, and the like, as required by various embodiments of the instant invention. As one skilled in the art will appreciate, though the memory is depicted as a single component, multiple different types of memory may be resent and the memory may also be a separate component or device connected to or in communication with the user computer (e.g., as remote storage). As such, in some embodiments, portions of the memory storing data may be implemented as network attached storage (NAS), storage area network (SAN), direct access storage (DAS), or any combination thereof, including, for example, multiple hard disk drives. Moreover, such data may be stored in one or more databases, tables or fields. As can readily be appreciated the specific storage utilized largely depends upon the data requirements of a specific application.

In the illustrated system, one or more such computing devices, run a behavioral processing program 108 which can be implemented as an application stored in the memory of the computing system to process various sensory data 103 and output some situational information (such as whether a face is present, amount of eye contact made, etc.) and/or a social cue, containing information about the social interaction recorded in the behavioral data, to an output such as a display, vibrotactile device, audio device, or some other device (104) in real time. A social cue is situation-dependent and can be based on multiple sensors. For example, video data from an outward-facing camera may be processed using a machine learning module (described in further detail in the description of feature (1) below) to recognize facial emotions in people in the wearer's field of view. Naturally, video data may refer to moving image data independent from its frame rate in any appropriate format such as RGB, grayscale, etc. and these data may contain depth information and may be captured from a variety of devices such as monocular or a multiview (e.g. stereo) array of cameras or infrared cameras. In one embodiment of the system, the head posture and/or eye gaze of the patient from accelerometer and/or eye tracking data are used to discover mutual gaze events occurring between the patient and other people and adapt the social cue based on these data. The details of methods that can be utilized in various embodiments of the invention are discussed below with reference to FIGS. 4-10. In one example illustrating the combination of different sensory data, using facial expression recognition in video data received from the outward facing camera, audio data processing in sound received from a microphone, and eye tracking in video data received from an infrared eye tracking camera, the behavioral processing engine can recognize that the patient is talking at length about a topic that may not interest his or her conversation partner any more, resulting in less and less mutual gaze and negative expressions. An appropriate social cue computed by the system here may be, "Pause: ask a question." In other embodiments, any of a variety of feedback cues can be generated by the behavioral therapy system as appropriate to the requirements of a specific application.

Figure 2:
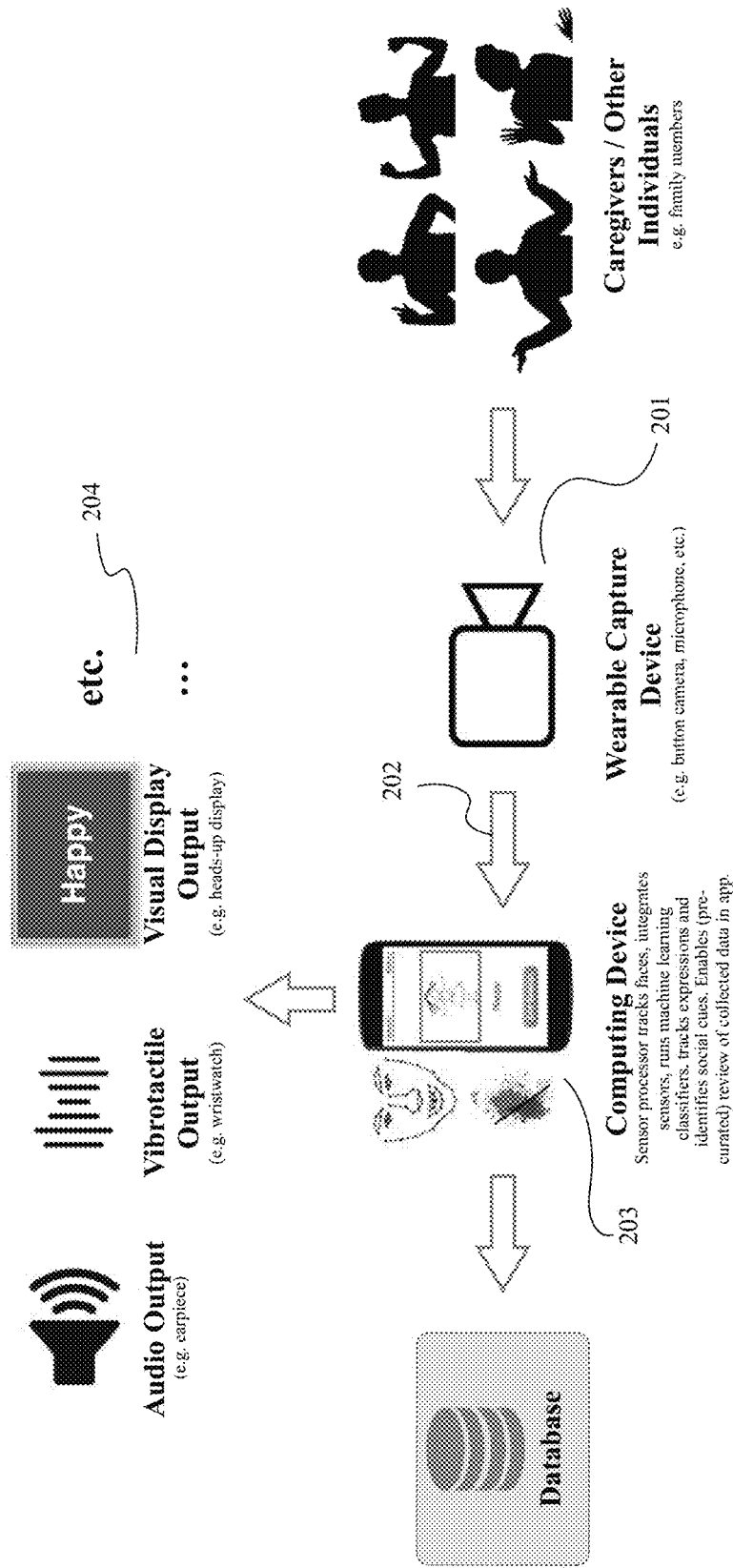
FIG. 2 shows a schematic overview of a behavioral system in which a wearable capture device provides egocentric video and other sensory data to a computing device in accordance with an embodiment of the invention.

FIG. 2 shows a schematic overview of a specific embodiment of the behavioral aid system in which a wearable capture device 201 provides egocentric video and other sensory data 202 to a computing device 203, which processes the data to recognize social actions (such as facial expressions) of people interacting with the patient as well as the patient's response to those actions and computes appropriate social cues (for example about emotions) that are in turn conveyed back to the patient through one or more output devices 204.

In general, in many embodiments of the present invention, a wearable device allows for at least one of video data capture (in the sense defined above) and/or providing feedback to the user (for example visual, through a heads up display or audio, through a bone-conducting speaker or earpiece). Common commercial examples that support both feedback and video capture include Google Glass, Vuzix M100, Epson BT-200, ODG R6, and Microsoft Hololens. Devices capable of delivering feedback only (and perhaps capturing audio or physiological data) include the Motorola Moto Hint, for example. The wearable device may or may not itself be a computing device in the sense described with FIG. 1 above.

Returning to the embodiment of FIG. 2, the patient wears the wearable computing device in a way that captures egocentric video from his or her point of view (for example, by chest or head mounting). The patient (also referred to as "wearer", "user", or "subject") generally is an individual with one or more behavioral challenges or mental disorders such as autism, anxiety, bipolar disorders, depression, schizophrenia, Alzheimer's, and Parkinson's disease using the system as part of some form of administered therapy, as a behavioral intervention, or as a learning aid. In some forms of therapy, the wearer may, however, be the caregiver rather than the individual with the mental disorder himself. The wearable obtains video and other sensory data 202, for example physiological data, such as heart rate, blood pressure, skin conductivity, etched measurements, and/or additional data of the patient's eyes through an eye tracker or the patient's face. In general, an "eye tracker" may be a hardware device used for monitoring the eye movements of a person interacting with the system that may use one more cameras, depth sensors, infrared lighting sources, and other components typically found in such devices aimed at identifying a pupil position and/or gaze direction. The eye tracker may be any commercially available system, like the Tobii Pro Glasses or SMI Eye Tracking Glasses 2, or could simply be a monocular camera (perhaps supplemented by an infrared-emitting light source). The eye tracker generates video data on its own which may be post-processed in software by the larger system incorporating the eye tracker (like in the case of the Pupil Labs Project eye tracker) or such processing may be implemented in the eye tracking hardware itself (like in the case of Tobii or SMI eye tracking systems).

The supplementary sensory data from various sources is transmitted along with the outward-facing video data to the computing device 203. Upon executing steps of a behavioral tracking program, a computed social cue is then transmitted to one or more output devices (which may include the computing device 203 and wearable device 201 itself, should they be capable of output) and outputted to provide real-time feedback to the patient and his or her caregiver.

In one specific embodiment of the system of FIG. 2, an egocentric camera (connected via wire or networking connection such as WiFi or bluetooth) can serve as an input device, while an earpiece (also connected via wire or networking connection such as WiFi or bluetooth) can serve as an audio output device. In this case, the mobile processing sends the appropriate output directly to the speaker in the earpiece.

Figure 3:
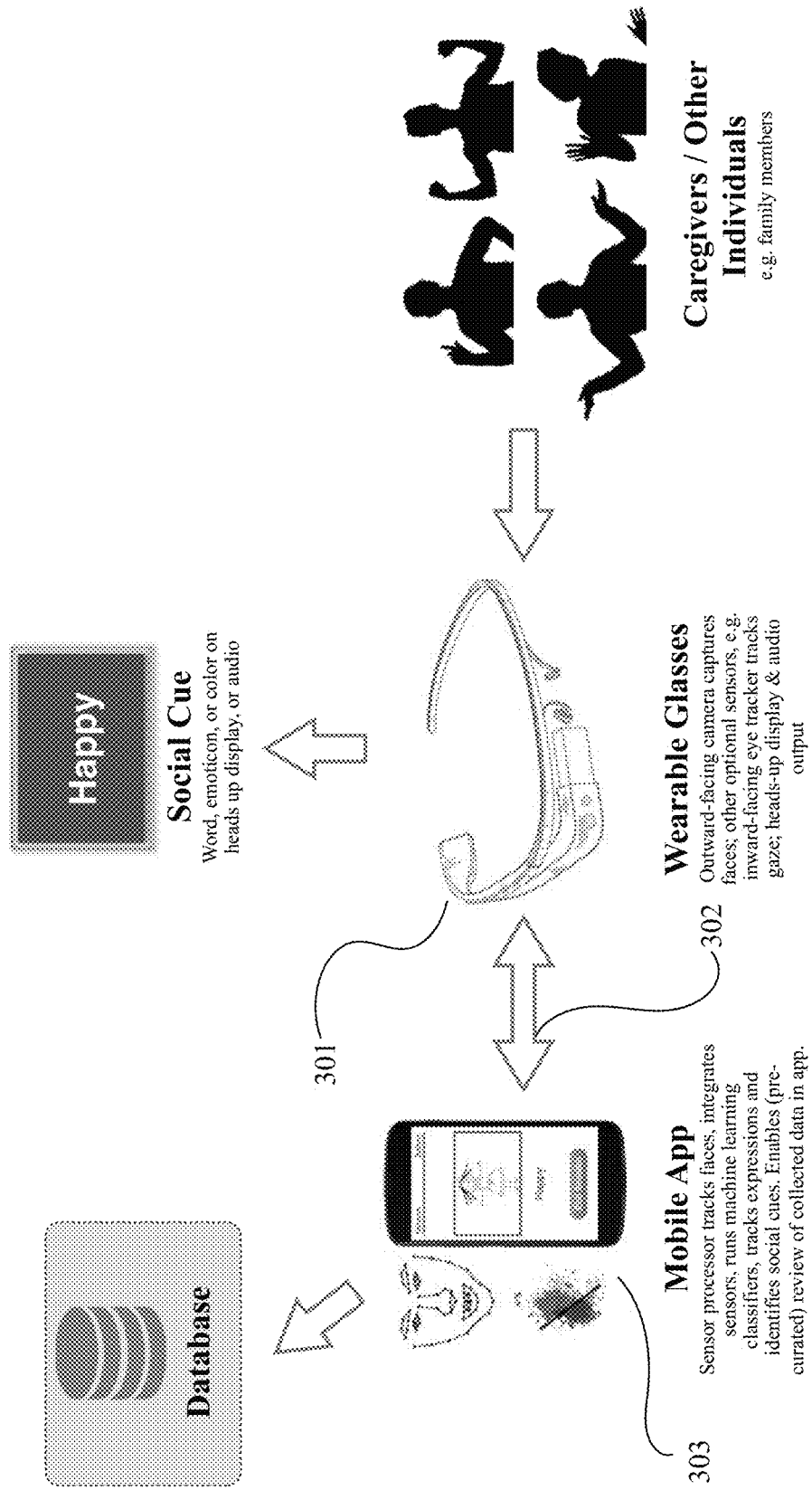
FIG. 3 illustrates a wearable capture device that is a pair of smart glasses that provides egocentric video and other sensory data to a mobile computing device in accordance with an embodiment of the invention.

In many embodiments, the wearable capture device may be paired with a mobile device that provides the computational resources for processing images being captured. FIG. 3 describes an embodiment in which the wearable capture device is a pair of smart glasses 302 that provides egocentric video and other sensory data 202 to a mobile computing device 303, which processes the data to recognize social actions (such as facial expressions) of people interacting with the patient as well as the patient's response to those actions and computes appropriate social cues (for example about emotions) that are in turn conveyed back to the patient through a heads up display or audio output of the smart glasses 302 and/or the mobile device 303.

Figure 12:
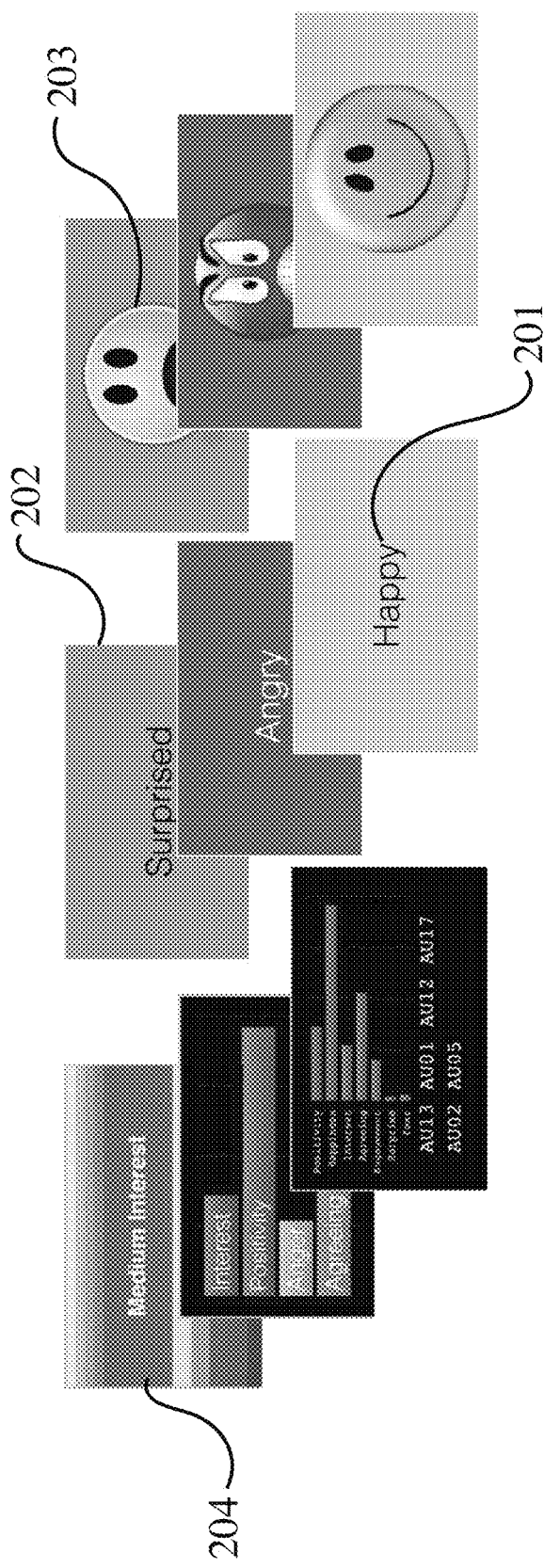
FIG. 12 illustrates various types of visual feedback that can be displayed in a heads-up-display in accordance with an embodiment of the invention.

This feedback can be designed in a way that other people (such as caregivers or patients) can notice or not notice it depending on the therapeutic goals. Referring to FIG. 12, visual feedback can, for example, consist of text 201, color 202, or an emoticon 203 or any combination of such displayed in a heads-up-display. Such feedback can be discrete (i.e. informative of a specific event) or changing over time (e.g. a score such as a "current interest level" score indicating to a patient the interest level of his or her conversation partner 204). Audio feedback includes a narrator reading out the name emotions or reading out specific cues, as well as a range of playful sound effects associated with emotions or other social cues. Depending on the hardware platform chosen as the wearable device, visual feedback can be extended to overlay information on the view of the world through holographic projection (e.g. when using a mixed reality system like Microsoft Hololens as opposed to Google Glass). In its simplest form, this takes the feedback "screen-driven" interfaces from FIG. 12 and projects them proximate to the person that the social cue is referencing. In a more complex embodiment of this approach, feedback about the social cues can be localized. For example, an emotional cue like "Happy" can highlight the individual expression by overlaying a figure on the mouth of a person and alerting the user to the locality of the expression. Feedback may also include confirmation that the wearer is currently seeing and engaged with a face, through visual, audio or vibratory cues. This may range from simply displaying whether and/or where a face is detected, to a more temporally sensitive measure indicating engagement with someone within the user's field of view, to directional, localized, or non-localized feedback that a user out of one's field of view may be engaged with. Said feedback may implicitly or explicitly convey a reward for engagement. Feedback may also include suggestions to the wearer for how to respond to certain social cues or situations as they occur.

Returning to FIG. 3, in addition to the real time social feedback, situational information can be transmitted back to the wearable device for use in an interface that involves a gamified activity, as described further below.

In both FIG. 2 and FIG. 3, the video and other sensory data may be transmitted in real time (using an appropriate transmission and perhaps compression model, while compression may want to be omitted for low-latency applications) or can be cached for future processing. Further, a version of any video data containing higher information density (i.e. color or resolution) of the video may be cached on the wearable for future transmission in addition to streaming lower-resolution frames for real-time purposes.

In many embodiments, the wearable device may include any of a variety of sensors, including in-ward and out-ward cameras, accelerometers, gyroscopes, a head-up display, and a microphone. A wearable glasses 301 that include an outward-facing camera, an accelerometer, a heads-up display, and/or microphone in accordance with an embodiments of the invention is illustrated in FIG. 3. An eye tracker can be attached to this device using a fixture that is connected via wire to either the wearable glasses or the mobile device. In certain embodiments of the system, the behavioral aid "unit" includes a pair of wearable glasses (such as Google Glass running the Android operating system) and a mobile phone (such as a Nexus 6), which are connected via a wireless network. The wearable glasses may act as a sensory input device for video and head pose data as well as an output device through a bone-conducting speaker, optional earpiece, and a heads-up display. To spare the limited battery life and processing power on the glasses, many of the computationally-intensive tasks such as frame processing, video encoding, and data storage may be handled on the phone. When users want to start or finish a new activity, they can use the mobile app, which may use a lightweight communications protocol to trigger the right activity on the wearable glasses and prompts the glasses to begin capturing camera frames at a rate of approximately 30 frames per second using a UDP packet stream. This can be implemented in a battery-efficient manner by spawning a hotspot on the phone and connecting the wearable glasses as a client to the WiFi network. When a new frame is captured, the full frame and other sensor data as well as a high-resolution image of the face area can be transmitted to the phone for processing. The phone may encode and store the video data in a parallelized fashion and/or run the frame through an expression recognition pipeline. It may then transmit a result packet including metadata about the face(s) tracked and expressions to the glasses. The glasses may interpret the result and show the appropriate social cue (either on the display or as audio). This process can happen in real time with less than 50 ms latency.

Figure 11:
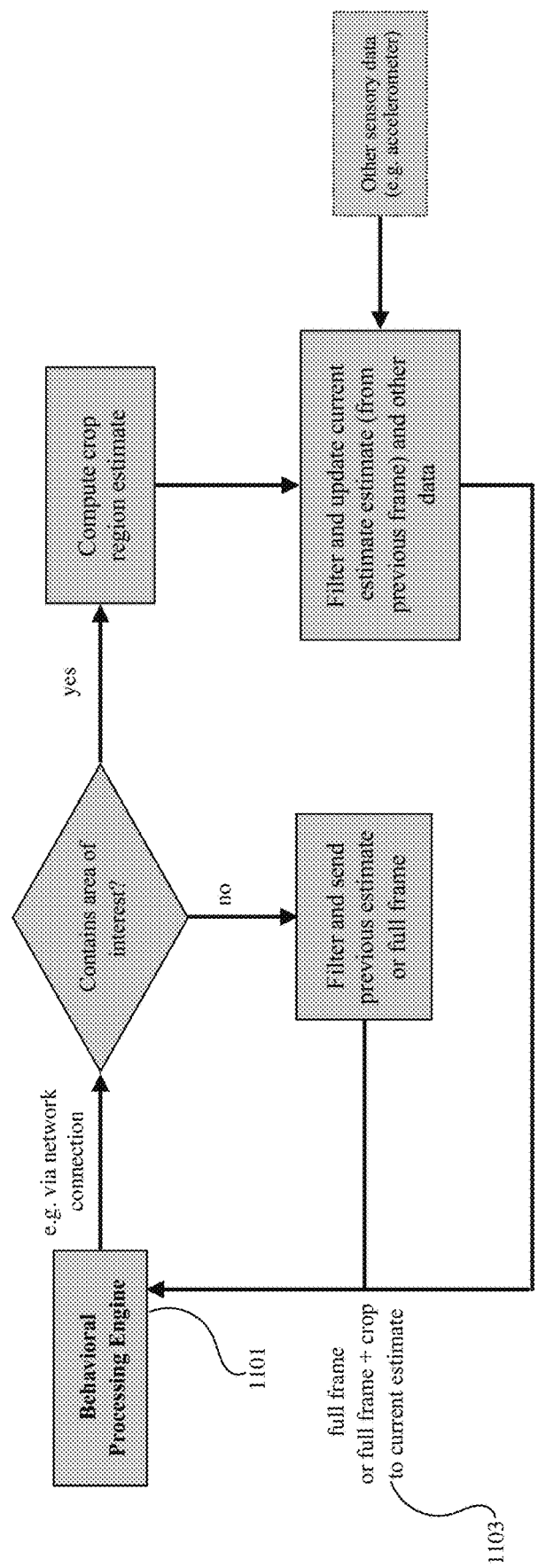
FIG. 11 illustrates a process whereby a packet stream of frames between the wearable glasses and the mobile phone may alternate between including a "full" face frame and a "zoomed in" frame in accordance with an embodiment of the invention.

Referring to the process described in FIG. 11, the packet stream of frames between the wearable glasses and the mobile phone may alternate between including the "full" face frame and a "zoomed in" frame that represents a certain region of interest (for example, a face) in higher resolution for more granular processing. On situational information input from the behavioral processing engine 1101 the process (which is easiest implemented on the wearable camera capture system in the specific embodiment of FIG. 3 or in any other computing device in the system in other embodiments consistent with FIG. 1), a region of interest (for example, given by fiducial points tracked in a face or by a bounding rectangle or other shape around the body of a person) is identified. Based on the temporal stream of these regions and possibly other associated data from the wearable device, a new estimated region of interest is computed, filtered, and a high-resolution crop to this region is sent back to the behavioral processing engine. In a simplistic embodiment of this method, the situational information sent includes the bounds of a tracked face. Based on these bounds, an initial crop of fixed frame size may be computed such that the face bounds are most centrally included in the frame. This is maintained as the "current estimate" and all frames are cropped to this estimate until the situational information contains an area of interest that is either outside of the current estimate in the original frame or does not contain an area of interest for some fixed number of frames. In another more complex embodiment of the system, a moving average or Kalman filter is used to "smoothen" a bounding region of interest around the current face estimate that is updated on every frame. As can readily be appreciated, any of a variety of processes can be utilized as appropriate to the requirements of a specific application in accordance with various embodiments of the invention.

Returning to the overall system architecture, various embodiments with functionally similar modifications of one high-level setup were described along with methods that enable one skilled in the art to implement these setups. Naturally, these can be extended further and should not be viewed as limiting. In various embodiments of FIGS. 2-3, various components of the system can be extended or omitted. In FIG. 2, for example, the wearable capture device and mobile processing unit may be the same device as opposed to two separate entities connected via a network connection (for example, one can think of a smartphone with an integrated camera). This severely simplifies the architecture of the system described in association since no networking is required to communicate between two distinct applications. However, it requires the use of a wearable computing device, capable of executing the processing required to implement (at least a subset of) the features described below. In yet another embodiment, the systems of FIGS. 1-3 may be extended with a computing device that is solely used as a "review station" to review data and insights gathered from the primary capture and real-time-feedback system (for example videos and behavioral statistics). In summary, a variety of commercially available hardware systems (as discussed above) can be employed in these embodiments, with tradeoffs in cost, functionality, and obtrusiveness, that may be appropriate for certain specific applications of the present invention, for example in behavioral therapy.

(1) Social Action Recognition System and Unstructured Social Cues:

While the previous section explained how to "wire up" such an engine into our system, this section focuses on creating a machine learning and data processing system that can be used to arrive at useful social cues.

Figure 4:
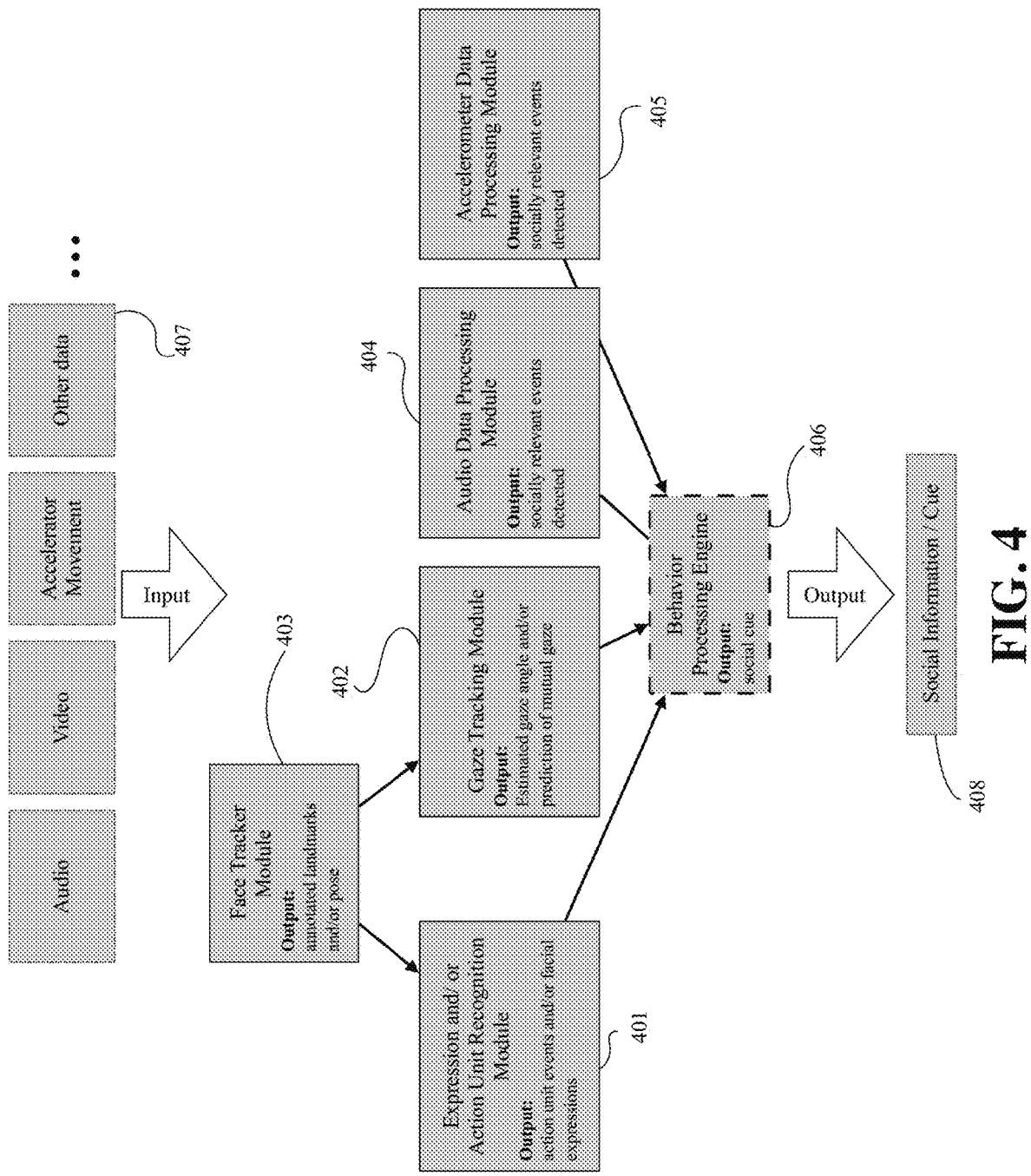
FIG. 4 illustrates a social action recognition system that can generate social cues from sensory data in accordance with an embodiment of the invention.

Referring to FIG. 4, a social action recognition system in accordance with an embodiment of the invention is illustrated that can generate social cues from sensory data. The illustrated embodiment relies on a data capture mechanism (audio, video, accelerometer, etc.) 407 which is then fed into a processing system that outputs social information 408 (facial expressions, facial muscle movements, body language, gestures, body pose, eye contact events, head pose, features of the conversation, fidgeting or other appearances of anxiety, etc.) relevant to the data delivered, executed in real-time on a data stream or offline on a set of data.

At a high level, the social action recognition system includes of an artificial intelligence system and a set of hardwired rules. The artificial intelligence (AI) system typically may include a series of pre-processing steps, a machine learning classifier, and a post-processing step. The output from the AI system may be passed to the "hardwired" system (here as part of the Behavior Processing Engine 406) which can implement a set of rules and outputs a final social cue.

These machine learning system components can generally be implemented as a regression or classification machine. In the regression case, the AI system most commonly yields continuous social cues (for example a "happiness" score). In the classification case, it typically yields an event-based cue (for example an "angry" moment). As known to those skilled in machine learning, depending on the implementation of the classifiers, the system can usually easily be configured to convert between these two types of cues. Outputted discrete and continuous cues is often treated differently in their feedback interfaces, as discussed in the previous section.

Several embodiments of the social interaction system may employ various sub-systems such as a face tracking module 403, an expression recognition module 401, a gaze tracking module 402, an audio processing module 404, an accelerometer data processing module 405 and a behavior processing engine that computes the final output, wired up as depicted in the figure. Naturally, any combination of these modules may be used depending on the application of the system.

Figure 5:
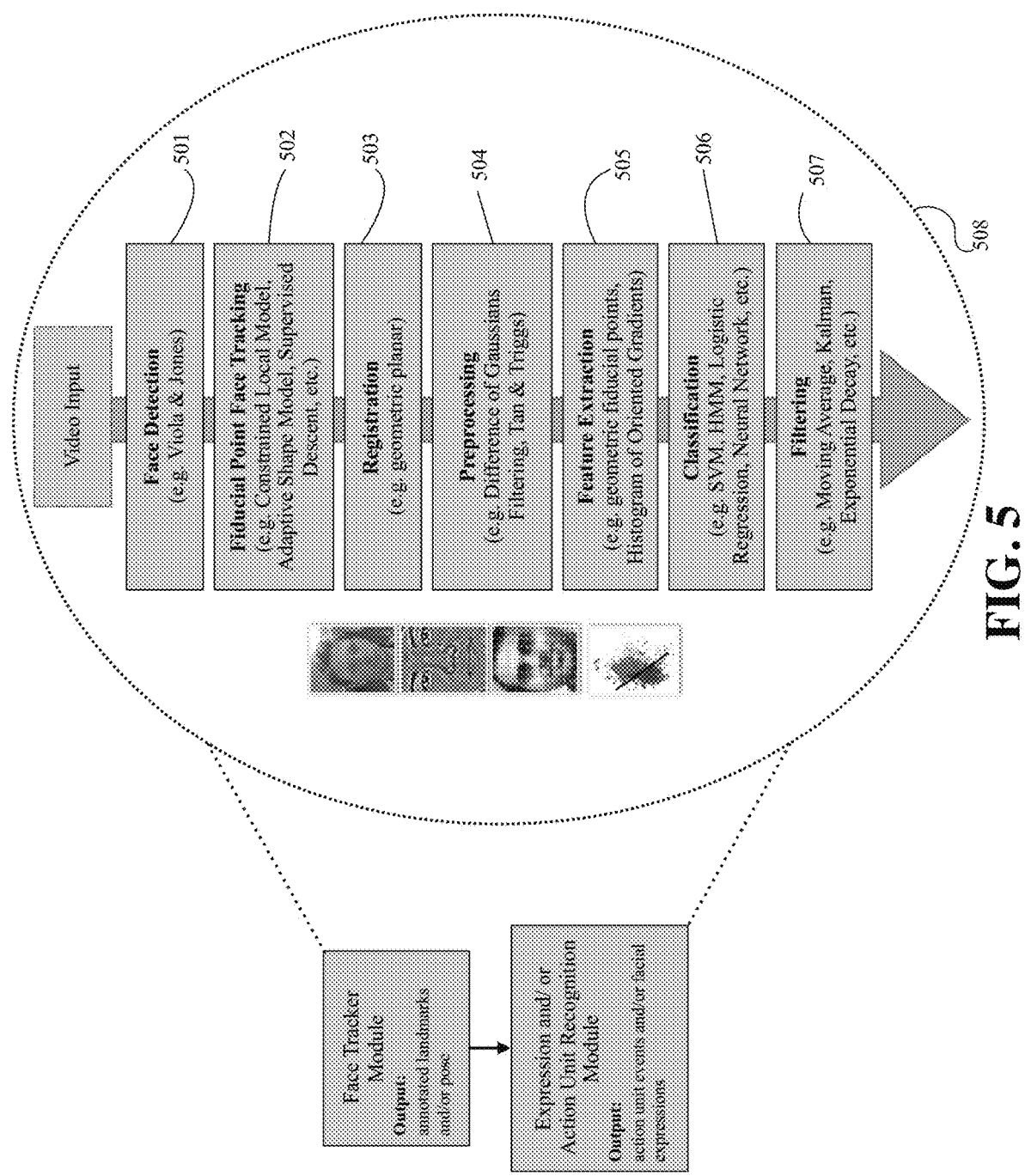
FIG. 5 provides a zoomed in view on an interaction of a face tracker and facial expression/action unit recognition processes utilized in accordance with an embodiment of the invention.

To describe these modules in the appropriate detail, it is helpful to consider their inputs and processes separately. Firstly considering the interaction of parts 403 and 401, FIG. 5 provides a zoomed in view 508 on the interaction of the face tracker and facial expression/action unit recognition processes utilized in a number of embodiments of the invention. Restricting attention to video data, input to the process is provided one image at a time, with the goal of outputting social information relevant to each frame. The methods described herein focus primarily on processing input from a monocular camera, but as one skilled in the art will appreciate, the proposed novel system can itself be extended by processing additional sensor input and still maintaining the processing, recording, and review structure described herein.

A process for identifying a facial expression or facial action may include the following pieces: (1) face detection 501 and/or (2) fiducial point face tracking 502, (3) registration of the face to a canonical size and pose 503, (4) lighting normalization preprocessing techniques 504, (5) Histogram of Gradients feature extraction in a region of interest about the face 505, (6) classification of the face's expression via a logistic regression classifier trained on image data 506, and (7) filtering of the resulting classification 507. One such processing pipeline is described in the paper "A practical approach to real-time neutral subtraction for facial expression recognition" by Nick Haber, Catalin Voss, Dennis Wall, Azar Fazel, and Terry Winograd, presented at the IEEE Winter Conference on Applications of Computer Vision (WACV), 2016 the relevant disclosure from which is hereby incorporated by reference in its entirety. FIG. 5 gives examples of how each one of these operations can be accomplished using approaches known in the literature. For example, registration in step (3) is an obvious geometric procedure, and lighting normalization in step (4) can be accomplished using the method of Tan, Xiaoyang, and Bill Triggs. "Enhanced local texture feature sets for face recognition under difficult lighting conditions." Image Processing, IEEE Transactions on 19.6 (2010): 1635-1650, the disclosure of which is hereby incorporated by reference herein in its entirety. A survey of alternate candidate algorithms for facial expression recognition that can replace the full pipeline 508 is given in the paper F. Dela Torre and J. Cohn: "Facial expression analysis." In T. B. Moeslund, A. Hilton, V. Krger, and L. Sigal, editors, Visual Analysis of Humans, pages 377-409, Springer London, 2011, the disclosure of which is hereby incorporated by reference herein in its entirety.

A number of methods to make these approaches practical in real-time situations in the context of the system described herein are described.

The first, termed neutral subtraction, described in detail below, and also described in the paper "A practical approach to real-time neutral subtraction for facial expression recognition," learns an estimate of the subject's neutral face features in real time and subtracts from extracted features. This has the purpose of enhancing robustness of the system over lighting and inter-subject variation.

The second consists of taking the frame-by-frame classification results of the expression recognition system and smoothing them across time: classification inherently has noise across time that can be mitigated by assuming some continuity across time, thus leading to a better user experience. Any algorithm that takes as input, at time t, all frames seen up until and including time t, and uses these data to make a prediction for time t, can be applied. Many embodiments of this involve simply keeping a fixed-size buffer holding the most recent sequence of frames and giving the user output only when a fixed fraction of the frames is classified to be the expression. In several embodiments, time dependence is explicitly added to the model through a Hidden Markov Model (for instance, see J. Wang, S. Wang and Q. Ji, "Early Facial Expression Recognition Using Hidden Markov Models," Pattern Recognition (ICPR), 2014 22nd International Conference on, Stockholm, 2014, pp. 4594-4599) the disclosure of which is hereby incorporated by reference herein in its entirety, or a Conditional Random Field (see, for instance, R. Walecki, O. Rudovic, V. Pavlovic and M. Pantic, "Variable-state latent conditional random fields for facial expression recognition and action unit detection," Automatic Face and Gesture Recognition (FG), 2015 11th IEEE International Conference and Workshops on, Ljubljana, 2015, pp. 1-8 the disclosure of which is hereby incorporated by reference herein in its entirety) and supply to the user the smoothed output provided by the model. In several embodiments, feed-forward convolutional neural networks are used in conjunction with recurrent neural networks such as LSTMs (Sepp Hochreiter and Jürgen Schmidhuber (1997). *Long short-term memory*, the disclosure of which is hereby incorporated by reference herein in its entirety. Neural Computation 9 (8): 1735-1780.) and GRUs (K. Cho, B. van Merrienboer, D. Bandanau, and Y. Bengio. *On the properties of neural machine translation: Encoder-decoder approaches*. arXiv preprint arXiv: 1409.1259, 2014, the disclosure of which is hereby incorporated by reference herein in its entirety), learning relations that generalize HMMs and CRFs. In particular, given the spatial dependence of the data, one embodiment may employ convolutional LSTM or GRU gates (such as those seen in Choy, Christopher B.; Xu, Danfei; Gwak, JunYoung; Chen, Kevin; Savarese, Silvio. *3D-R2N2: A Unified Approach for Single and Multi-view 3D Object Reconstruction*. Eprint arXiv:1604.00449, 04/2016, the disclosure of which is hereby incorporated by reference herein in its entirety), adapting these convolutional recurrent methods directly to the task of expression recognition from sequences of frames. Learning an appropriate model depends on the more specific user interactions expected, and as such, such embodiments would require particular models learned through data gathered in these therapeutic use cases.

One particular smoothing issue systems in accordance with many embodiments of the invention may address is that of expression recognition while talking: standard algorithms give undesirable feedback when the subject is talking due to small, quick variations in expression during talking. While much may be mitigated by the above smoothing efforts, several embodiments of the system involve explicit screening (no output given) when the subject is recognized as talking. This may be accomplished by training visual time-dependent classifiers explicitly aimed at recognizing video sequences where the subject is talking. Several embodiments involve using audio signals to tell when the subject is talking. Certain embodiments rely on training time-dependent classifiers (e.g. Conditional Random Fields, or recurrent neural networks) to recognize not only standard facial expressions but "neutral talking," "happy talking," "sad talking," and so on. Time dependent models in this context can be helpful, as a primary issue when handling data in which a subject is talking is that, in any given frame, the subject may have an expression that would be interpreted differently were it held for a longer period of time. Such time-dependent models could be trained with video data of standard facial expressions along with expressive talking sequences.

Broadly, better user experience is to be had when the system is biased to predict a neutral expression (and, for instance, give no feedback) when unsure, and the algorithms above can have a built-in "neutral bias," which can be achieved by tuning the standard parameters of the classifiers.

Figure 6:
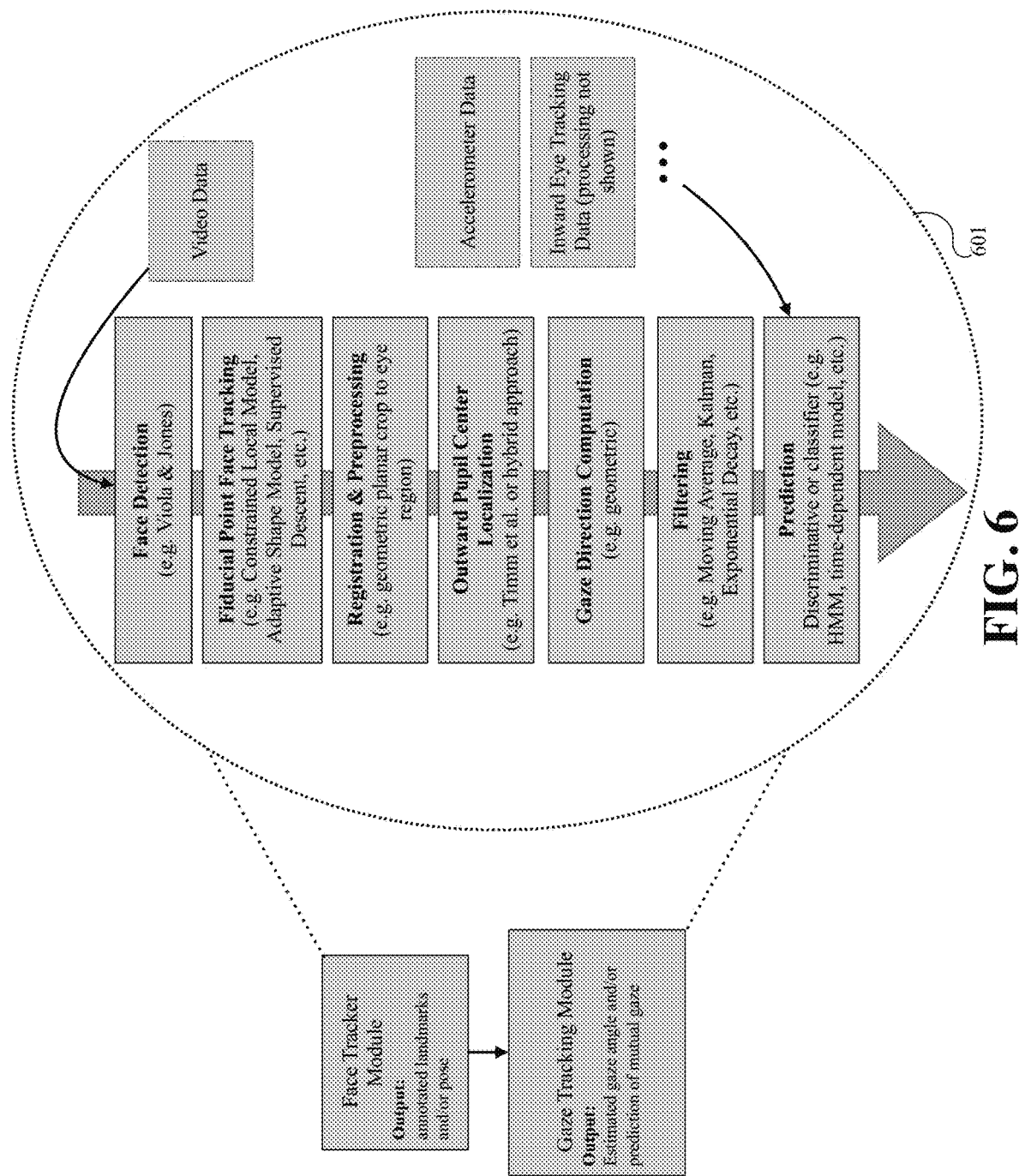
FIG. 6 illustrates a process for integrating outward-facing video data and possibly inward-facing eye tracking data to detect mutual gaze or one-way gaze events that may result in social cues in accordance with an embodiment of the invention.
Figure 7:
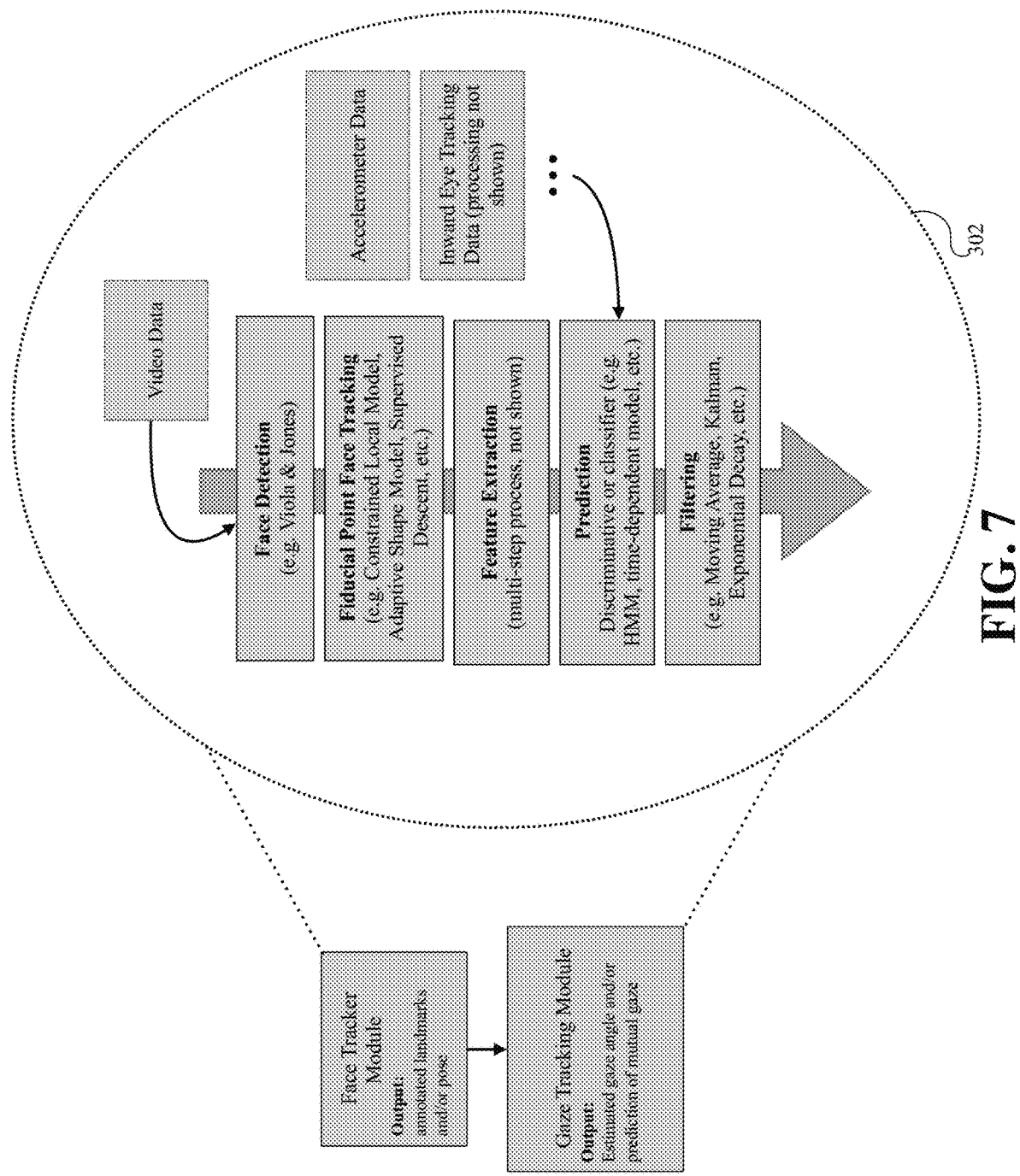
FIG. 7 illustrates a process for integrating outward-facing video data and possibly inward-facing eye tracking data to detect mutual gaze or one-way gaze events that may result in social cues in accordance with an embodiment of the invention.
Figure 8:
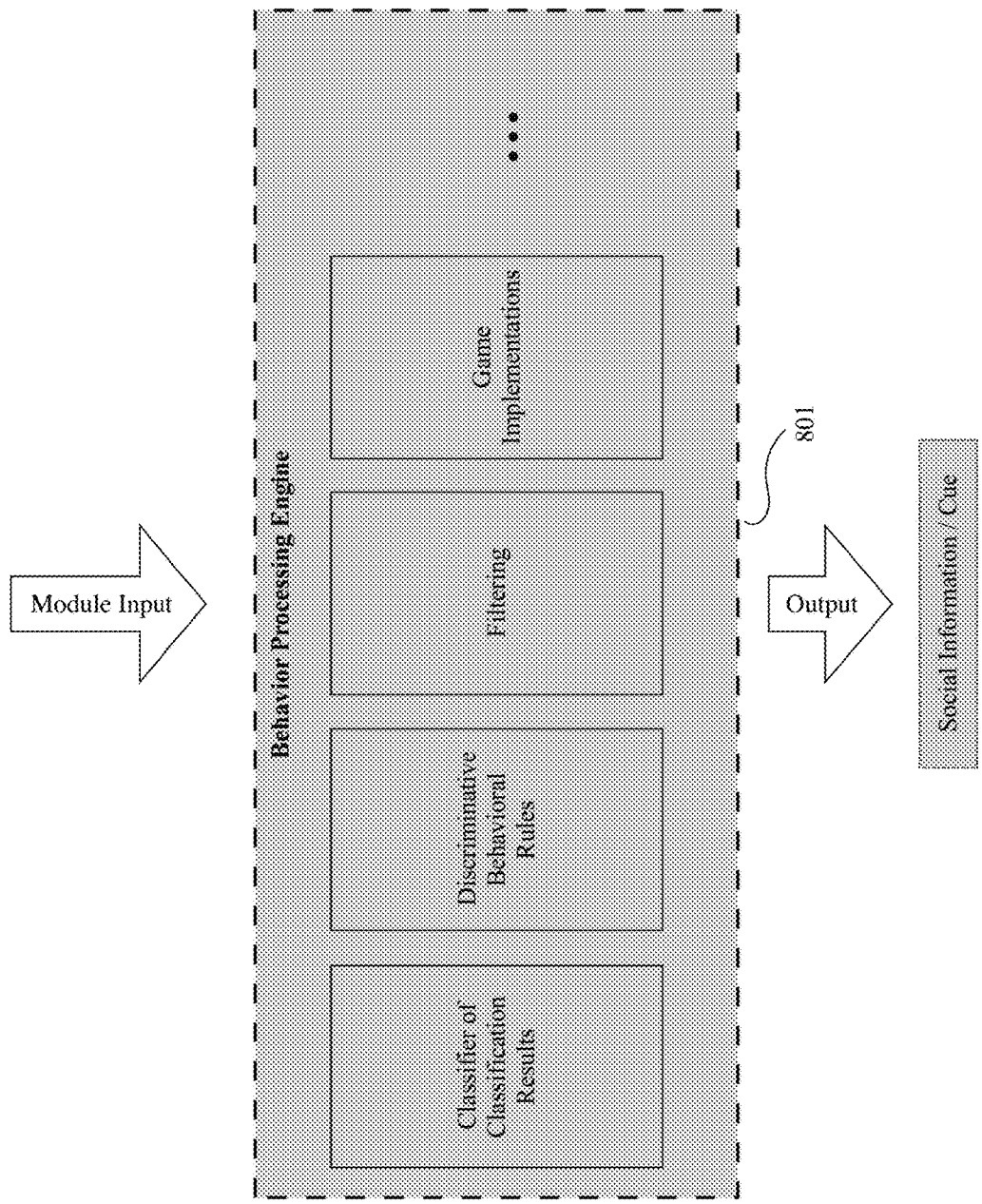
FIG. 8 illustrates a system that produces social information or a cue to be given to the wearer and other users of the device in accordance with an embodiment of invention.

Many embodiments detect gaze events using one or more inward-facing eye tracking data in conjunction with outward-facing video data. Moving on to module 402, FIGS. 6 and 7 give two methods for integrating outward-facing video data and possibly inward-facing eye tracking data to detect mutual gaze or one-way gaze events that may result in social cues in accordance with an embodiment of the invention. Like with facial expression recognition, both methods involve detecting, tracking, registering, and preprocessing facial image data. The method of FIG. 6 relies upon a geometric approach, where gaze of the wearer and of a tracked subject in front of the wearer are simultaneously estimated, relative to each of their positions, which are estimated as well. This combines such data to produce a prediction of mutual gaze events. The method of FIG. 7 can use a machine learning classifier directly, combining the data of extracted features from the outward subject (fiducial points, texture features, neural network output) along with features from the wearer (eye tracking, accelerometer measurements) along with true values of (mutual) gaze events in order to learn a predictor for these events. Pupil tracking can be done in a variety of ways in real time; see, for instance, (Timm, Fabian, and Erhardt Barth. *Accurate Eye Centre Localisation by Means of Gradients*. VISAPP 2011—Proceedings of the Sixth International Conference on Computer Vision Theory and Applications, Vilamoura, Algarve, Portugal, 5-7 March, 2011, the disclosure of which is hereby incorporated by reference herein in its entirety) as well as the open source project (Pupil Labs. http://pupil-labs.com/pupil/. Accessed 2 May 2016.)

Moving on to module 404, many embodiments of the system may integrate audio signals, and the system may provide feedback after analyzing expressive content, for instance, using the successful time-dependent models explored in M. Wöllmer, A. Metallinou, N. Katsamanis, B. Schuller and S. Narayanan, "Analyzing the memory of BLSTM Neural Networks for enhanced emotion classification in dyadic spoken interactions," Acoustics, Speech and Signal Processing (ICASSP), 2012 IEEE International Conference on, Kyoto, 2012, pp. 4157-4160 the disclosure of which is hereby incorporated by reference herein in its entirety. One version of this may simply provide expression recognition cues based only on tone, whereas another may augment this by paying attention, to some limited extent, to content of conversation. In all cases, audio signals may be recorded by any of the constituent devices and streamed/synchronized with visual information and fed into the classification device.

Moving on to module 405, accelerometer data from various locations (head-mounted, arm-mounted, etc.) can be incorporated into the social interaction recognition process by detecting specific socially relevant events such as obsessive behavior (shaking, repeated movements, etc.) or gestures (head shake, head nod, head move forward, etc.). Many wearable systems provide "gesture recognition APIs" that are suitable for such purposes, but more complex machine learning systems can be used to enable this type of recognition. A variety of suitable approaches for turning temporal accelerometer data into gesture classifications are described in the academic literature and the specific processes utilized are largely dependent upon the requirements of a given application. Further, accelerometer data may be used to extract physiological data such as heart rate measurements directly or in conjunction with other sensors. The paper (J. Hernandez, Y. Li, J. M. Rehg and R. W. Picard, "BioGlass: Physiological parameter estimation using a head-mounted wearable device," *Wireless Mobile Communication and Healthcare (Mobihealth)*, 2014 EAI 4th International Conference on, Athens, 2014, pp. 55-58, the disclosure of which is hereby incorporated by reference herein in its entirety) illustrates how to do this and gives proof of concept, showing that such a system can perform robustly in real-life situations. These data can be used by the behavioral processing engine 406 in conjunction with other data to enable game play (e.g. reward a user for mimicking expressions like a head nod) or change social cue output (e.g. avoid sending too many social cues during a time of sensory overload/obsessive shaking).

Finally, all of this can be integrated in Behavior Processing Engine 406. Depicted in FIG. 8, the system can combine the results of all above systems and produce social information or a cue to be given to the wearer and other users of the device. The system can use one or more of the following components: (1) facial expression recognition (of action units, universal expressions, and/or more complex expressions), in the form of classifier and regression affect models that take as input video data (visual and/or audio), (2) discriminative behavioral rules, (3) an implementation of a game enabling social interaction (described in Game Applications below), (4) gaze tracking, (5) head pose/accelerometer data, (6) mutual eye gaze models, and (7) filters of the above for the production of smooth outputs across time. The system then decides on relevant social information or cues to provide to the wearer or other users (one embodiment being in the form of a game, where multiple physical components are simultaneously interfaces to the users).

Directing attention back to broader social action recognition, many of the systems described for facial expression recognition can be extended to more complex action recognition than basic emotions in faces.

Beyond the face and audio, the system may also incorporate body language and pose information in order to give social cues, relying on our own classification systems as well as highly developed work on activity recognition. This may employ recent advances in tracking pose such as the paper M. Dantone, J. Gall, C. Leistner and L. Van Gool, "Human Pose Estimation Using Body Parts Dependent Joint Regressors," Computer Vision and Pattern Recognition (CVPR), 2013 IEEE Conference on, Portland, Oreg., 2013, pp. 3041-3048 the disclosure of which is hereby incorporated by reference herein in its entirety, using the same video stream used for facial expression recognition. Using pose information and other cues gotten through the video feed, the system can feed data into various highly developed systems for activity recognition (see, for instance, R. Bodor, B. Jackson, and N. Papanikolopoulos. Vision-based human tracking and activity recognition. In Proc. of the 11th Mediterranean Conf. on Control and Automation, June 2003, the disclosure of which is hereby incorporated by reference herein in its entirety, as well as M. K. Fiaz and B. Ijaz, "Vision based human activity tracking using artificial neural networks," Intelligent and Advanced Systems (ICIAS), 2010 International Conference on, Kuala Lumpur, Malaysia, 2010, pp. 1-5, the disclosure of which is hereby incorporated by reference herein in its entirety). The system may also take said video data and above mentioned expression recognition to infer more complex emotional states (using, for instance, the algorithm covered in R. El Kaliouby and P. Robinson, "Mind reading machines: automated inference of cognitive mental states from video," Systems, Man and Cybernetics, 2004 IEEE International Conference on, The Hague, 2004, pp. 682-688 vol. 1, the disclosure of which is hereby incorporated by reference herein in its entirety), such as anxiety, boredom, or attentiveness, over longer periods of time, delivering social cues after it has noticed such a state over a longer period of time. These can be combined with other sensors, including but not limited to, gaze tracking and accelerometer, in order to combine knowledge of the surrounding world with knowledge of the wearer in order to tailor feedback accordingly.

Figure 10:
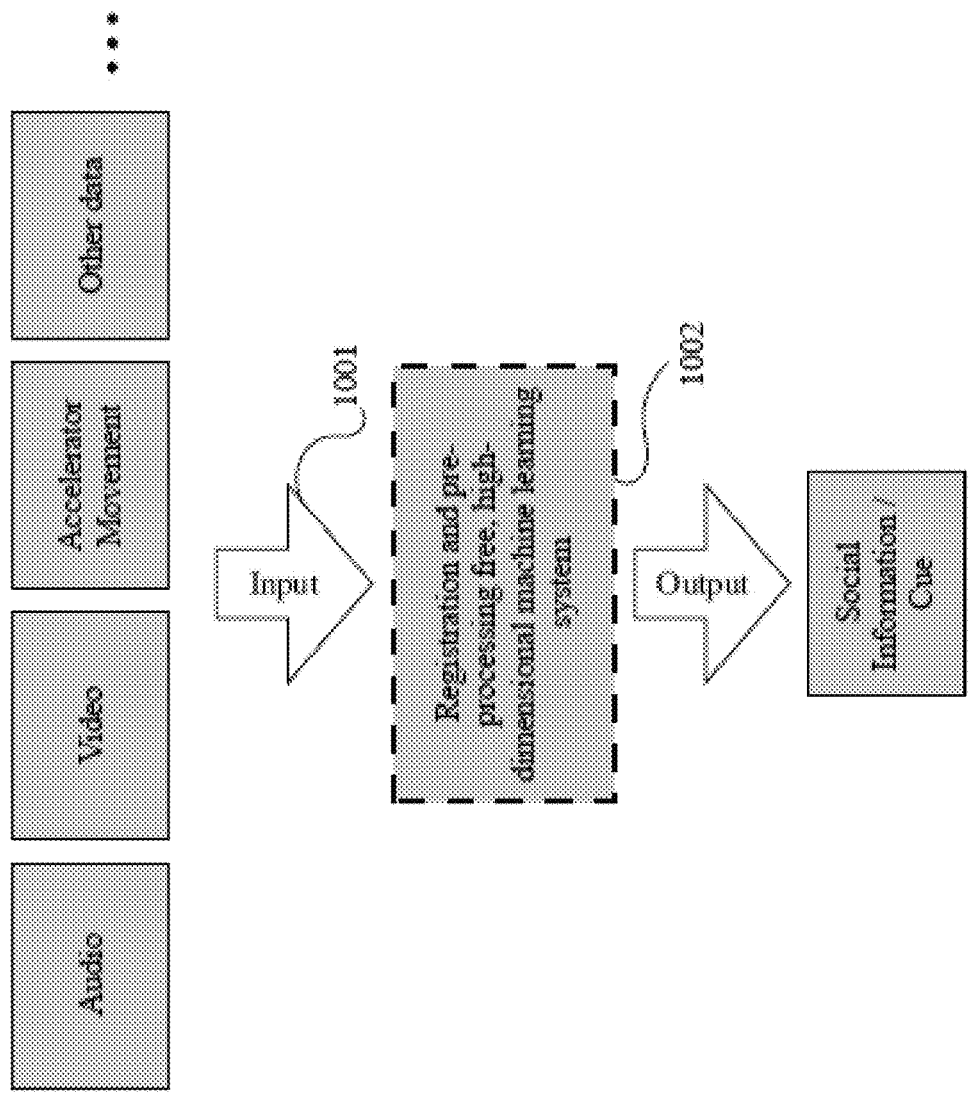
FIG. 10 illustrates an example of a high dimensional machine learning system in accordance with an embodiment of the invention.

Returning to the social interaction recognition system of FIG. 4, in many embodiments, the various sub-components of this system may be replaced with a single registration and pre-processing free, high-dimensional machine learning system. An example of a high dimensional machine learning system in accordance with an embodiment of the invention is illustrated in FIG. 10, where upon input 1001, a single machine learning system may predict social information and/or cues directly from a concatenation of the various input data. Various deep convolutional neural network architectures, starting with AlexNet (Alex Krizhevsky, Ilya Sutskever and Geoffrey E. Hinton. *ImageNet Classification with Deep Convolutional Neural Networks*. Advances in Neural Information Processing Systems 25. Pages: 1106-1114, 2012, the disclosure of which is hereby incorporated by reference herein in its entirety) and the more recent GoogLeNet (Christian Szegedy, Wei Liu, Yangqing Jia, Pierre Sermanet, Scott Reed, Dragomir Anguelov, Dumitru Erhan, Vincent Vanhoucke, Andrew Rabinovich. *Going Deeper With Convolutions*. The IEEE Conference on Computer Vision and Pattern Recognition (CVPR), 2015, pp. 1-9, the disclosure of which is hereby incorporated by reference herein in its entirety), both widely available architectures, have shown the ability to perform object recognition, segmentation, and localization tasks without any registration or image preprocessing. Transfer learning can then be applied to the domain of affective computing with a small amount of data. These architectures can be taken to generate features that can then be fine-tuned and used in any of the above recurrent neural network (conv-LSTM or GRU as well as general LSTM and GRU) architectures. Another embodiment uses Scattering Convolutional Neural Networks (see Joan Bruna and Stephane Mallat. Invariant Scattering Convolution Networks. arxiv.org/pdf/1203.1513, 2012, the disclosure of which is hereby incorporated by reference herein in its entirety).

In many embodiments, the system may also employ a variety of strategies to calibrate social action recognition on users, including calibrating expression recognition in order to account for inter-subject differences. This may involve the capture of data on specific individuals, which may be gotten through several modes, including data capture events for the calibration purpose and data previously captured in the execution of the social action recognition system. In many embodiments, the system may then query one or more users in order to determine ground truths. This can be a key ingredient in improving the accuracy rate of a general classifier in the social action recognition system to outperform state-of-the-art rates on specific individuals (such as a patient's family or group of caregivers). Once the data, either labeled or unlabeled, has been gathered on a target family, the system can broadly apply domain adaptation methods—which aims to increase accuracy on a target distribution of data (the target family) given little data from the target distribution and much data from a source distribution (everybody else). The careful balance that is to be struck through any of these techniques is that the model should perform well on the data gathered on the target group of caregivers (e.g. the user's family) but is also generally robust, as any data collection effort on one given family cannot take into account all lightings, changes in appearance, and inclusion of other individuals in activities with the system. Many embodiments provide a simple tuning of weight parameters through a stochastic gradient descent on the general model learned—which may utilize a careful selection of algorithm parameters (such as learning rate and regularization term) that is domain-specific and is reached at through data. Several embodiments use a hierarchical Bayesian approach, wherein different families can have models trained with different weights, but subject to the condition that each family's weights is drawn from a common distribution. This has the effect of automatically supplementing knowledge from one family's data with knowledge from everyone else's data. Both of these approaches may have the distinct advantage that, upon capture of data on the target family, the model can be adapted on the device without any resources beyond the general model, which may be compactly stored on all devices. This can allow for a quick calibration. Certain embodiments of the system may utilize the greater resource of all data used to train the general model, and hence either all data could be kept locally, or computation can be done in cooperation between the local device and an outside computing resource (such as by uploading the data to the outside computing resource or doing computations in parallel with regular communication). This embodiment may use all data, supplementing the target data with weighted source data (most off-the-shelf machine learning algorithms, such as SVMs and logistic regressions, support data weighting, and any algorithm can be made to do so by resampling data proportional to weights), the weights can be determined by a relevance criterion between the source data and target data. One such relevance criterion can be found in Y. Q. Miao, R. Araujo and M. S. Kamel, "Cross-Domain Facial Expression Recognition Using Supervised Kernel Mean Matching," Machine Learning and Applications (ICMLA), 2012 11th International Conference on, Boca Raton, Fla., 2012, pp. 326-332, the disclosure of which is hereby incorporated by reference herein in its entirety.

In many embodiments, upon a machine-learning classification and arrival at a social cue, various post-processing techniques can be used to keep the number of false positives at a minimum and reduce the potential therapeutic harm that can arise from misclassifications.

Firstly, the number of cues provided may be kept to a minimum using a filtering algorithm, such as a moving average filter, a low-pass time-domain filter, or other suitable model, to reduce the sensory overload possibly associated with a large number of cue alerts.

Further, to address the challenges of noise coming from the behavioral processing engine, systems in accordance with several embodiments of the invention use a visual indicator on the wearable device to indicate to the patient when the system is functioning properly based on obtaining a confidence score from the behavioral processing engine, such that a patient can tell the lack of a cue from a potential false-negative cue. In a mixed reality system, the social cue may be localized to a particular face, for example an arrow pointing to that face or a circle around the face or a particular part of it.

(2) Game Applications:

Given the overarching architecture description and part (1) of the system in accordance with many embodiments, one skilled in the art can easily appreciate how part (2) can be implemented across the wearable and mobile hub device and part (3) can be implemented on the mobile device alone.

In many embodiments, given a social action recognition system and communications infrastructure, the mobile-wearable system can serve as a platform for a variety of games that enable social interaction. In many embodiments of the system, such games are triggered by the caregiver on the mobile device and then start up on the wearable device. The wearable device may stream data frames to the mobile device as described above and use "situational information" extracted from the behavioral processing streamed back from the mobile device to guide game play logic. Gameplay prompts can be conveyed through a variety of feedback mechanisms (audio, visual, etc.) just like other social cues discussed above. For example, patients wearing the wearable device get rewarded for engaging in eye contact with other people. A higher score or some other kind of reward may be achieved when the social action recognition system recognizes face-to-face eye contact with high probability. In another example, a patient may be rewarded for mimicking a certain social action, such as a head nod.

In another example, the caregiver may choose emotions to reenact, and the wearer is rewarded for guessing them correctly. Score tracking and levels of increasingly complex or subtle emotions may be used to extend the engagement of the wearer as their recognition of the reenactments improves. In other examples, games may be triggered by the wearer as opposed to the caregiver, by trackpad input, voice command, or other methods. For example, the wearer may be encouraged to wear the wearable over an extended period of time and "collect" faces or emotions whenever they might see them, giving the wearer increased control over gameplay. In several embodiments, games used on the platform may involve the use of various location detection technologies (including but not limited to, GPS technology) to place or find items of interest in certain locations in a treasure hunt style fashion. The variety of games offered may also include methods by which the wearer and caregiver may collect scores across the games and track their overall progress over time. The wearer and/or caregiver may also be presented with opportunities to personalize the user interface of the system as a reward system for the completion of a number of sessions of the variety of games offered.

(3) Review Application:

The data review application in accordance with many embodiments of the invention takes data gathered through the engagement of (1) and presents it in a manner that can be reviewed by the wearer and those interacting with the wearer through the engagement of (1).

Figure 18:
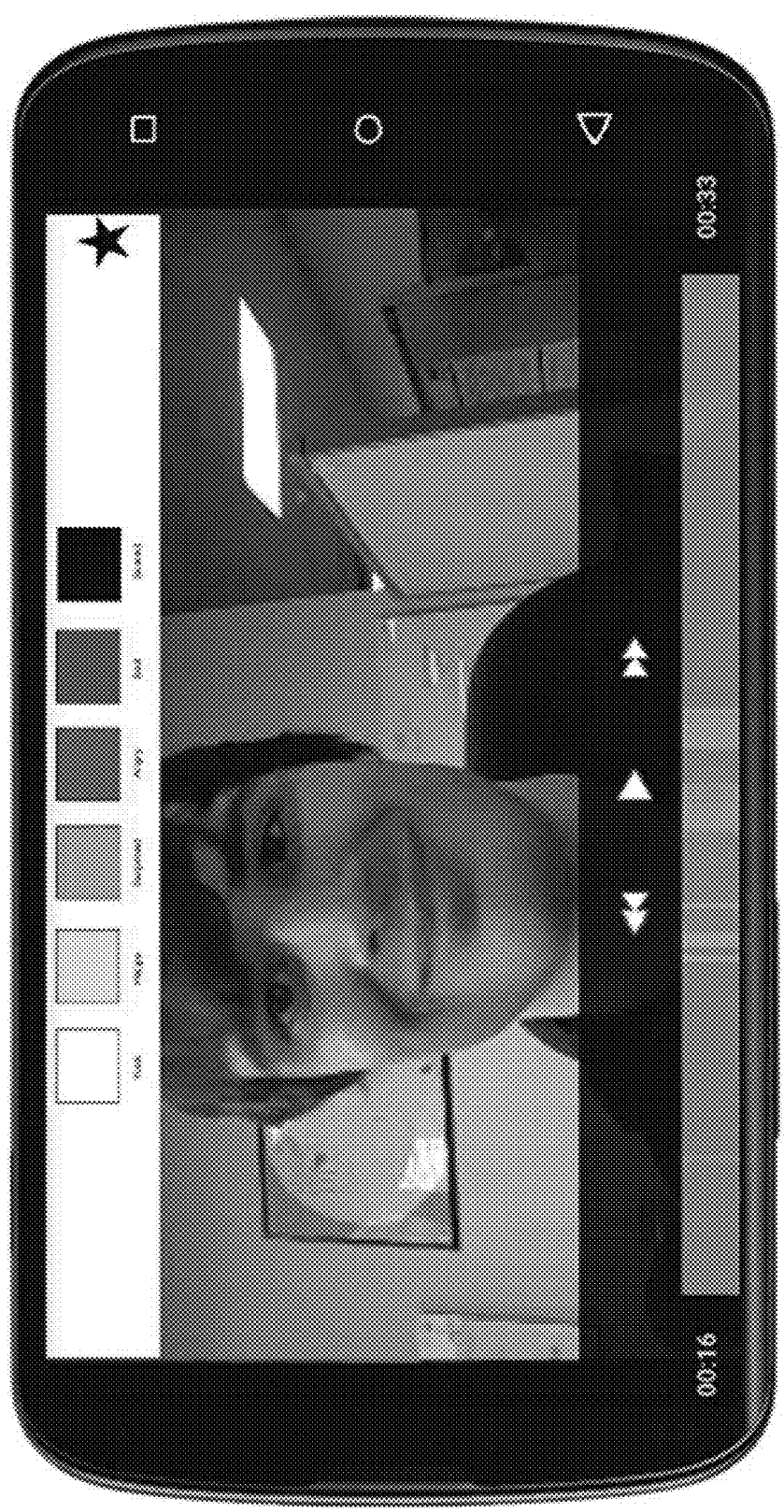
FIG. 18 illustrates a UI whereby a review application allows users and caregivers to review activities recorded throughout the day in accordance with an embodiment of the invention.

Referring to FIG. 18, in certain embodiments, the review application allows users and caregivers to review activities recorded throughout the day. Videos may be presented with "emotional moments" auto-curated and highlighted in an interface which allows users to visualize their appearance in the videos (including information on type of social action recognized) and jump to them for viewing. The emotional highlights can be extracted using the methods described above. In one example therapeutic setting, caregivers are encouraged to review these moments with their patients (and if they choose, potentially, behavioral therapists and/or other caregivers).

Figure 13:
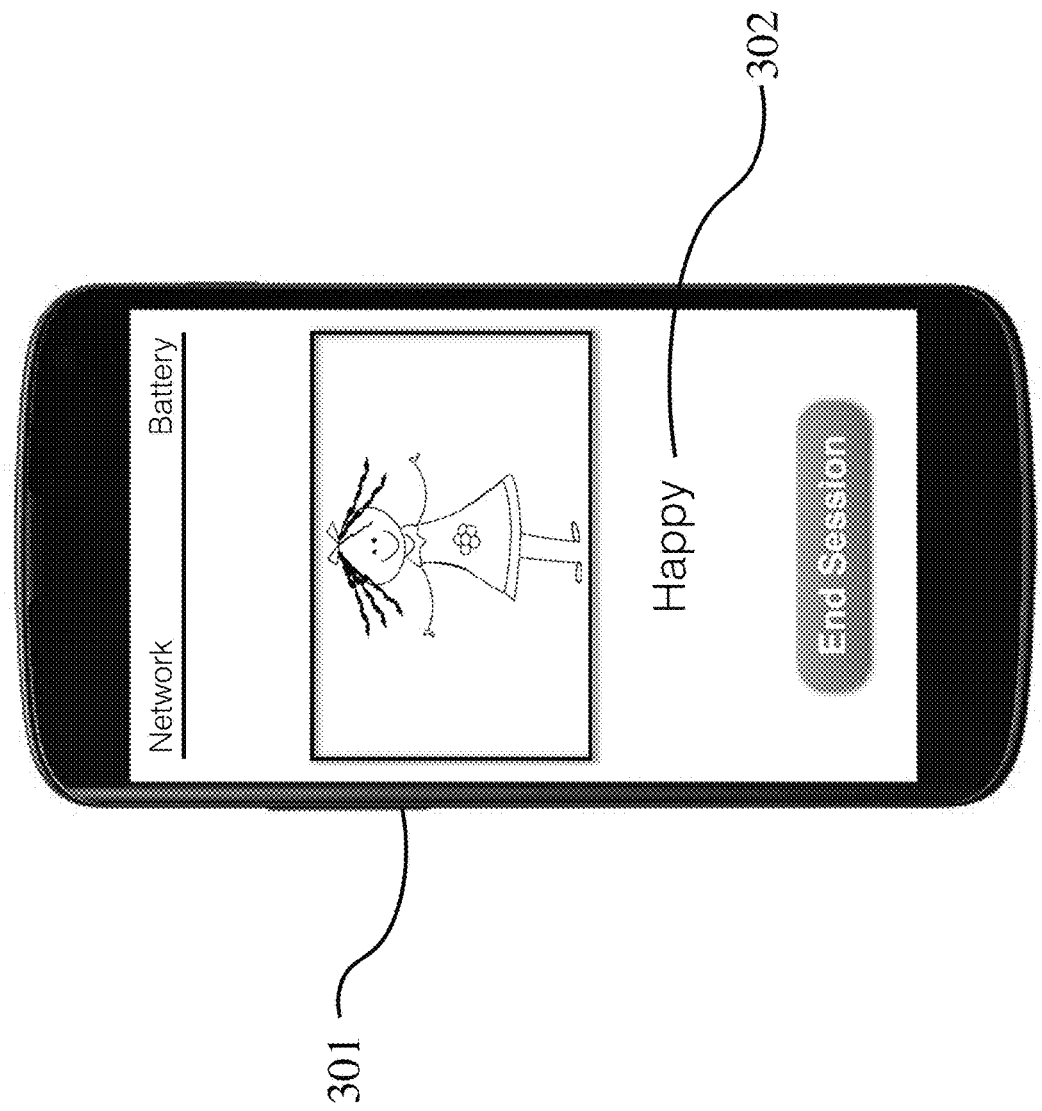
FIG. 13 illustrates an application executing on a mobile device providing an indication of an emotion being detected for a person in accordance with an embodiment of the invention.
Figure 14:
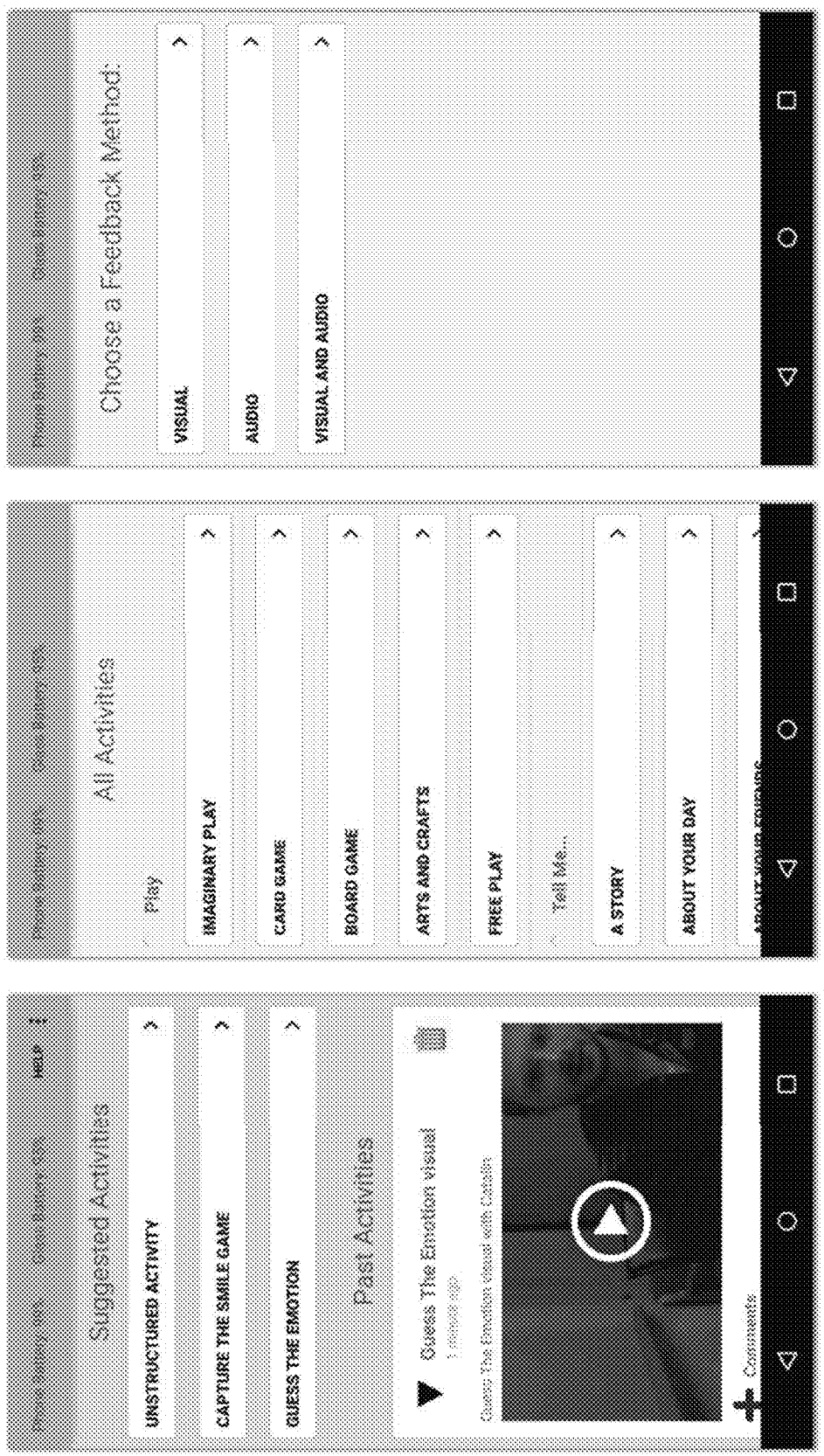
FIG. 14 illustrates a review system that may contain a newsfeed-like view of the previous session recordings in chronological order in accordance with an embodiment of the invention.
Figure 15:
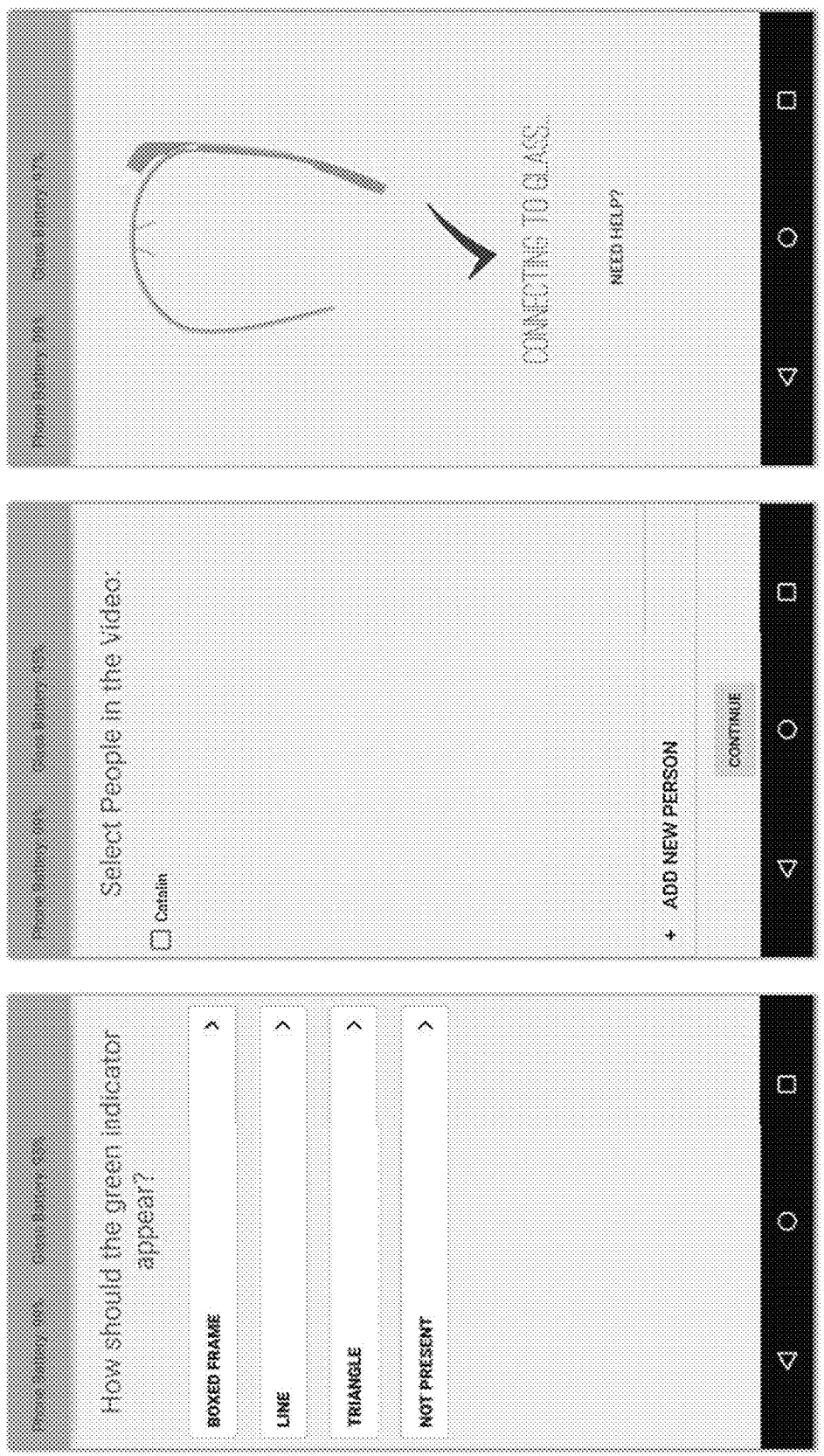
FIG. 15 illustrates several UIs for selecting various settings of the application in accordance with an embodiment of the invention.
Figure 16:
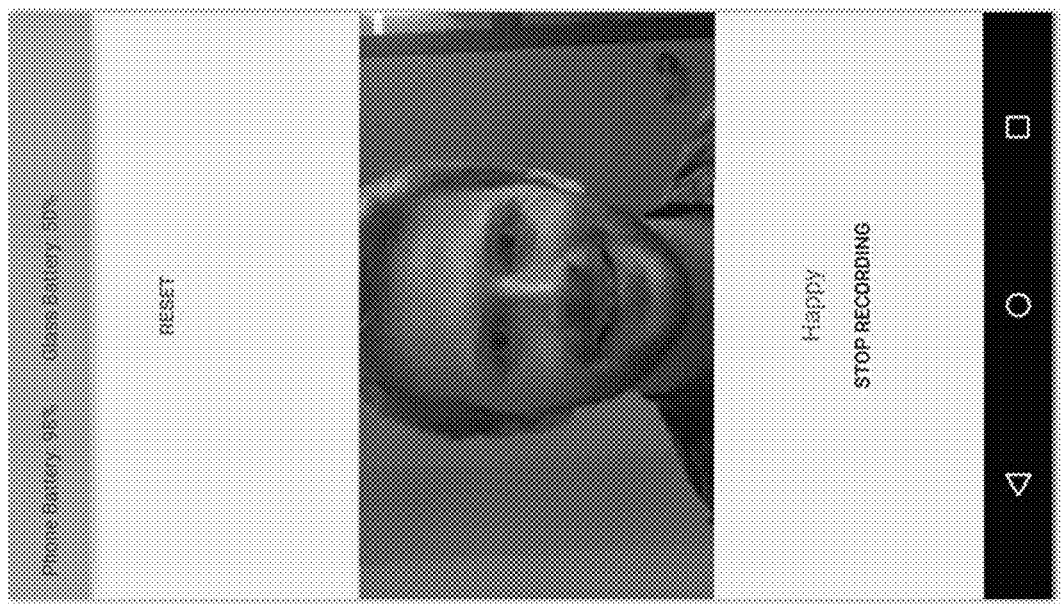
FIG. 16 illustrates an application executing on a mobile device providing an indication of an emotion being detected for a person in accordance with an embodiment of the invention.

In certain embodiments, the parent review system is a mobile application that runs on the same phone as the social behavior processing program that performs the computationally intensive emotion recognition. FIG. 13 and FIG. 16 illustrate an application executing on a mobile device 301, providing an indication of an emotion 302 being detected for a person in accordance with an embodiment of the invention. As depicted in FIG. 14, the review system may contain a newsfeed-like view of the previous session recordings in chronological order. Users of the review system have the ability at any time to view, hide, or permanently delete videos from the newsfeed. FIG. 15 illustrates several UI interfaces for selecting various settings of the application in accordance with an embodiment of the invention.

In certain embodiments, the review system may take the form of presenting short video clips immediately after a video session, representing only the auto-curated "emotional moments", and asking the wearer and/or caregiver to review them as part of finishing the session. This could further integrate and enable the tasks described in (4) Online and Active Learning. The emotional moments could also be revisited and relabeled by child or caregiver at any time via a photo roll-like view, allowing the opportunity for additional labeling data over time.

Statistical data extracted from video and sensory outputs can be stored in this application may be transmitted to an additional server for off-loaded processing. Such data and resulting statistics (which may be computed remotely or on the mobile device) can be presented in various visualizations (such as pie charts, graphs, etc.) as progress measures and/or achievements.

(4) Online and Active Learning

Figure 9:
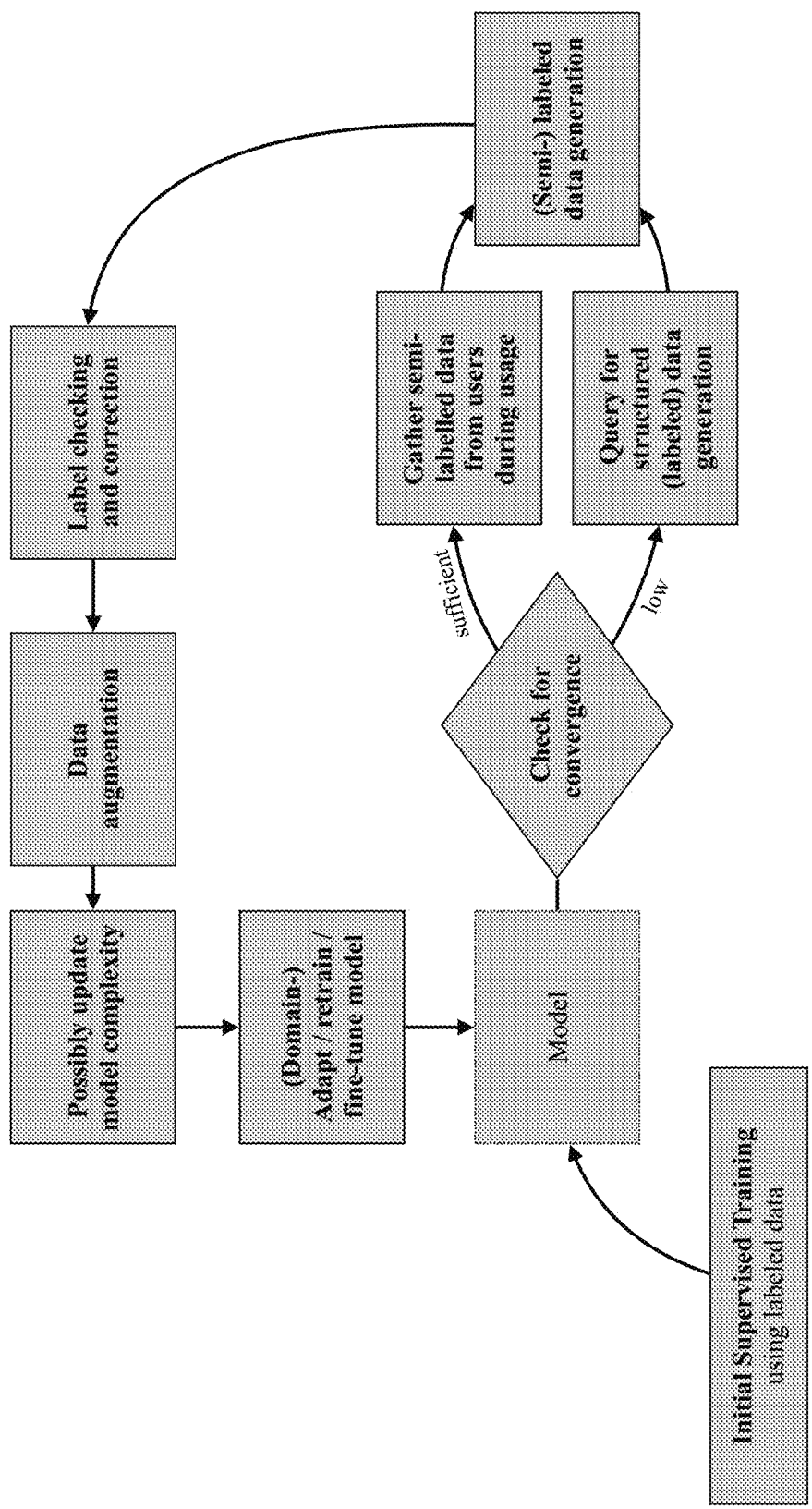
FIG. 9 illustrates a process for label correction of training data for use in training classifiers in accordance with an embodiment of the invention.

Referring to FIG. 7 and FIG. 9, the machine learning systems generally employed by systems in accordance with many embodiments of the invention can be set up to query users in a variety of ways in order to better the model. In several embodiments of such a query is to ask users, after a therapeutic usage of the device, whether various instances were classified correctly—this can double to serve as a learning tool for the user, as well. In this way, the images and/or video sequences that captured the expression can be annotated with ground truth information and relied upon for training updated classifiers. Several embodiments of such a query is to ask users or support staff to correct dataset labels. In both cases, queries may be administered via a simple graphical display on any piece of the system or a separate console, in which images or a sequence of images are displayed in still or video format, along with a question of the form "Is the current expression _____?" with the option to change the expression from the prediction. In both cases, it is infeasible to ask humans to manually correct labels frame-by-frame, so these embodiments may take an active learning perspective (see Burr Settles, *Active Learning*, Morgan & Claypool, 2012 the disclosure of which is hereby incorporated by reference herein in its entirety), which rely on a variety of heuristics to select data to be used in these queries. These heuristics include selecting data with maximum posterior entropy (given a probabilistic classifier) or a query-by-disagreement, in which several classifiers are simultaneously used and users are queried when sufficient disagreement is to be had. As data is structured with a time-dependence, queries often take some sense of continuity or smoothness into account across time. In certain embodiments, such a process is to simply enforce small blocks of consecutive data points to have the same label. Several embodiments involve the adaptation of techniques from text information extraction—for details, see Aron Culotta, Trausti Kristjansson, Andrew McCallum, and Paul Viola. *Corrective feedback and persistent learning for information extraction*. Artificial Intelligence, Volume 170 Issue 14-15, October, 2006, Pages 1101-1122, the disclosure of which is hereby incorporated by reference herein in its entirety. Many processes train a Conditional Random Field model using time-dependent data, and, querying the user using a confidence estimate gotten by their "constrained forward-backward" algorithm, label corrections can be propagated across the time domain via their "constrained Viterbi" algorithm. Upon correcting labels, the model can be updated using these data with new labels. This comes in two flavors: the local update of a model used by the device that made the queries to the user (in the case that the end-user answered queries), and the global model off which local models adapt. In the local case, any of a variety of heuristic criteria (change in entropy, fraction of time wrong, for instance) can be used to decide to retrain or update the model locally or globally, using any of the domain adaptation methods covered in (1). In the global case, the deployed systems may periodically transmit data which saw a correction to a central computing resource, and the data augments general training data for the global model. Upon updating the global model, the new model parameters may be transmitted to deployed systems. This can be extended beyond Conditional Random Fields to apply to many time-dependent models of expression recognition, including recurrent neural networks.

Figure 17:
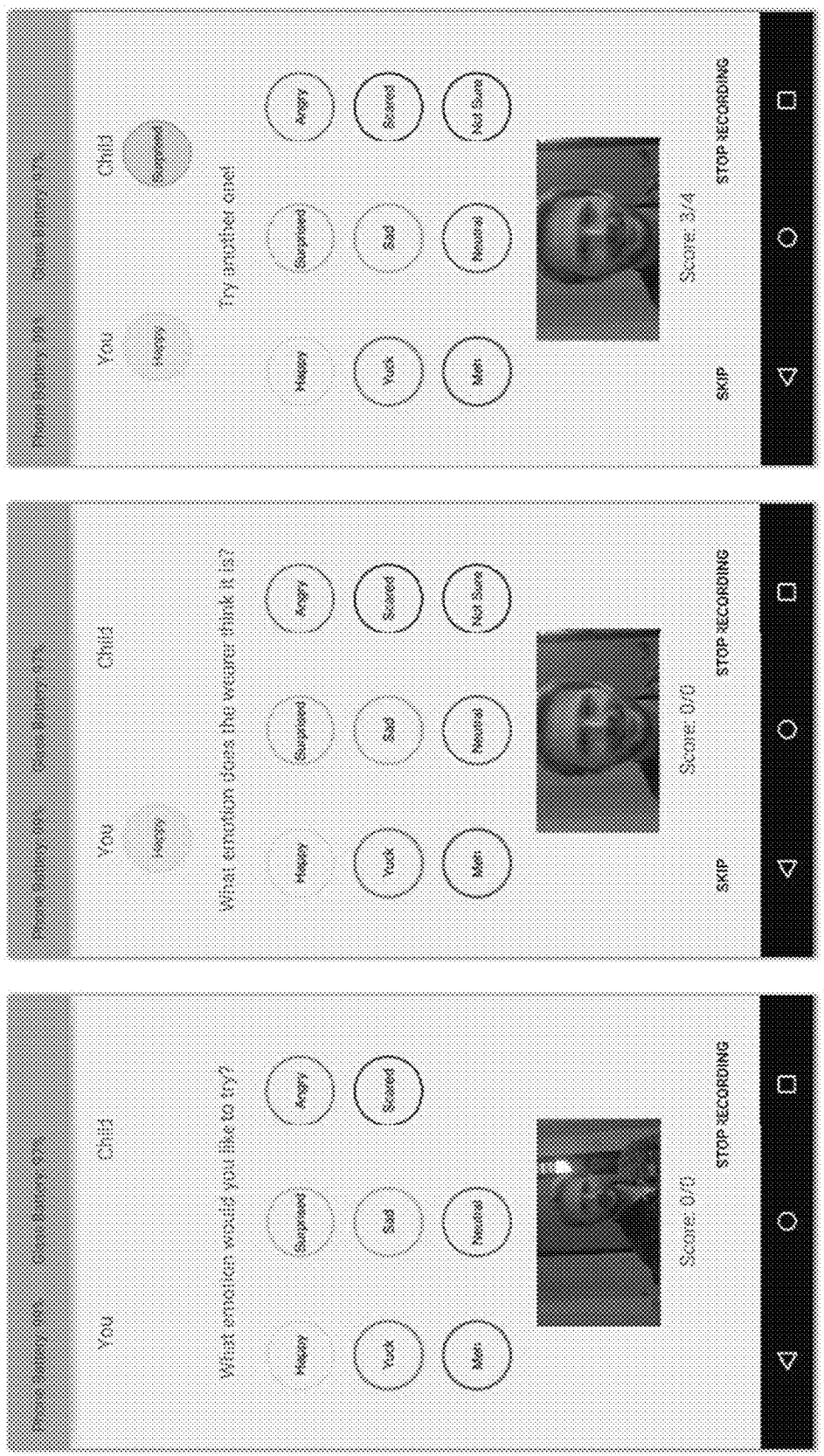
FIG. 17 illustrates various UIs of a mobile device executing a behavioral therapy system in accordance with an embodiment of the invention.

A data labeling/feedback mechanism mentioned in the preceding paragraph can be an integration with a game/outcome measure that queries users to recognize expressions as a measurement of this skill. Referring to FIG. 17, delivered through a computer or phone interface, the outcome measure can ask the user and caregivers to identify expressions found in data—the frames queried can be a mix of faces the algorithm is fairly certain about (giving unambiguous examples for the users to evaluate) and faces the algorithm is fairly uncertain about—as measured by entropy or query-by-disagreement strategies mentioned above, for example—in order to give data points useful for the improvement of the expression recognition classifiers. The use of multiple labelers (child and caregivers) giving several signals can reduce error, and a module that measures the reasonableness of the labels (using the level of agreement of human labelers in conjunction with machine learned algorithms) can decide whether a further expert labeler should determine the true value of the expression, the human input should be taken as true value, or the data should be discarded.

Neutral Feature Subtraction

Methods for automated facial expression recognition—identifying faces as happy, sad, angry, etc. —typically rely on the classification of features extracted from images. These features, designed to encode shape and texture information, may depend on both (1) the expression an individual is making, and (2) the individual's physical characteristics and lighting conditions of the image. To reduce the effect of (2), some approaches establish a "baseline" for an individual and subtract out this individual's baseline neutral feature. This extra neutral feature information often is not available, in particular, for in-the-wild, real-time classification of a previously unseen subject. Thus, in order to implement "neutral subtraction", many embodiments estimate an individual's neutral features. Furthermore, many embodiments extend neutral subtraction to different computer vision feature spaces as a method to correct for inter-face and lighting variance. Many embodiments further provide a simple, real-time method that is robust to class imbalances and in principal works over a wide class of feature choices.

Many embodiments utilize an approach that does not require the training of a complex subject-specific model, and thus can adapt to a new subject in real time. In particular, let $x_s$ be the subjects feature random variable, and let $V_s$ be the (hidden) feature of the subject's neutral (non-expressive face). If $$x_s = f(v_s, \delta_e) \quad (1)$$

where $\delta_e$ is a subject-independent variable which instead depends on the current expression e, then expression recognition can be reduced to (1) estimating $v_s$ for the subject and (2) learning a classification model $\delta_e \mapsto e$. In particular, if the simplifying assumption is made that $$x_s = v_s + \delta_e, \quad (2)$$

then, assuming that there are estimates $\bar{v}_s$ for $v_s$, train and test on neutral subtracted features $$\hat{x}_s = x_s - \bar{v}_s. \quad (3)$$

Equation (2) is in general a linear approximation. There is reason to believe this to be a good approximation for many appearance features under the preprocessing treatment (Section "Baseline: Feature Extraction" discussed below, first, lighting normalization, some embodiments may compute features on aligned images that allows the standard arguments for background subtraction to apply. Thus, features such as HOG and SIFT can perform well. This makes intuitive sense for geometric features: if some subspace of the feature space gives the distance between the eyebrows and nose, then not this quantity, but rather the difference between the current distance quantity and the quantity in a neutral state may correlate best with an expression such as surprise. The same intuition can be applied to a variety of feature spaces. Appearance-based features such as SIFT and HOG can yield a classifier which pays attention to the appearance of lines on the forehead, and such a classifier might decide that a subject with wrinkles is perpetually angry. Neutral subtraction allows for correcting this. It is reasonable to expect that it can aid appearance-based features with a variety of variations, including lighting, skin tone, and to some extent, facial hair.

Contribution

Many embodiments provide a simple process to estimate $v_s$ for each subjects and classify frames with expressions, delivering expression classification in real time. In many embodiments, the process takes as input a neutral/expressive (2-class) classifier, trained on the raw features ($x_s$) of all frames, as well as an expression classifier (including neutral, hence 7- or 8-class) on the neutral-subtracted features, where $v_s$ is estimated as the mean of all features with neutral as true value. At runtime, the 2-class classifier may allow the process to get an initial estimate of the neutral feature and to continually update that estimate.

In many embodiments, this process has a number of advantages. First, it may provide outputs in real-time with little processing delay, requiring no complex subject-specific model to be trained. While performance may vary, it may be independent of the input classifier types used and may require no probabilistic output from the classifiers. It may also in principle be agnostic to a wide variety of geometric and appearance features. Furthermore, as described below, in many embodiments, it is shown to perform well with HOG features. Training and evaluation may be done on a frame-by-frame basis and place no strong demands on data above the needs of the input classifiers (and may not require that all training subjects have examples of all classes). Lastly, it may limit the extent to which class imbalance at test time affects the neutral feature estimate.

An objection may be made that including "neutral" as a class in the classification task may boost accuracies with a neutral subtracted model: a simple thresholding on the norm of the neutral-subtracted feature works well for classifying an example as neutral or non-neutral. However, (1) in real-time expression recognition, recognizing the neutral face may be important, as a subject often will not be expressive in even conversational settings and (2) experiments conducted reveal that for more difficult classification tasks, the overall effect of neutral subtraction may be substantial even when the classification task does not include "neutral". A proposed process for real-time neutral feature estimation and subtraction along with experimental results are described below.

Real-Time Neutral Feature Estimation and Subtraction

Given a classification task of mapping images to labels Y of expression. Let the number of classes be K. In many embodiments, the process takes as input a K-class expression classifier F trained on neutral-subtracted features, as well as a 2-class neutral/expressive classifier $G_e$ trained on raw (not neutral-subtracted) features. To be more precise, given training data $\{(x_{s,i}, y_{s,i}) | s \in S, i \in I_s\}$ with s parameterizing subjects and $I_s$ indices for the frames of subject s. At training time, for each subject, the process may compute the mean neutral feature $$\bar{v}_s = \frac{1}{N_s^n} \sum_{y_{s,i}=neutral} x_{s,i} \quad (4)$$

where $N_s^n$ is the number of neutral features for subjects. Many embodiments may then compute $\hat{x}_{s,i} = x_{s,i} - \bar{v}_s$ for each frame. F may be trained on the preprocessed data $\{(\hat{x}_{s,i}, y_{s,i}) | s \in S, i \in I_s\}$, with any choice of algorithm. To train a general expressive classifier $G_e$, many embodiments may use the raw features $x_{s,i}$ for all s and i available, and alter the labels to be neutral if $y_{s,i}$ is neutral, and expressive otherwise. In training these classifiers, depending on the learning method used, many embodiments may need to pay attention to balance and undersample/oversample/weight one or multiple classes.

At test time, many embodiments are given a stream $(x_{s,i})_{i=1}^N$, of features for subjects, in chronological order. Many embodiments may allow a buffer period, during which no predictions are made and instead all frames may be classified with $G_e$, taking the mean of all frames labeled as neutral as a first estimate of $v_s$. This buffer period can be chosen in several ways—for example, after a set number of features labeled as neutral have been seen, or after the mean of the features labeled as neutral sees a change of less than a certain threshold. In many embodiments, simply setting a number of frames to be seen before ending the buffer period, corresponding to a couple of seconds, may achieve high accuracy. In the algorithm illustrates in FIG. 19, many embodiments summarize this decision by Buffer($(x_{s,i})_{i=1}^{j}$, $G_e$), where j is the current frame, returning true if the process is still in the buffer period and false if the buffer period can end.

After the buffer period—i.e., at frame $j_{buff}$—the process in many embodiments may go back and make predictions for frames 1 to $j_{buff}$ using estimate $\bar{v}_s$: $F(x_{s,j}-\bar{v}_s)$ gives these predictions. After this, for every feature $x_{s,j}$ that is seen, the process may update the estimate of the neutral feature. This can be done in a number of ways. In many embodiments, the simplest version is simply to update the mean $\bar{v}_s$: if $k_n$ is the number of neutral features seen before $x_{s,j}$, and the process has estimated $\bar{v}_s$ for the neutral feature, then if $G_e$ classifies $x_{s,j}$ as neutral, the process may simply update $$\bar{v}_s \leftarrow \frac{k_n \bar{v}_s + x_{s,j}}{k_n + 1} \quad (5)$$

and increment $k_n$ by one; if $x_{s,j}$ is not classified as neutral, no update is made. If $G_e$ gives a probabilistic output, then many embodiments can take an expectation of $v_s$, weighting all features seen by the probability each is neutral.

Figure 19:
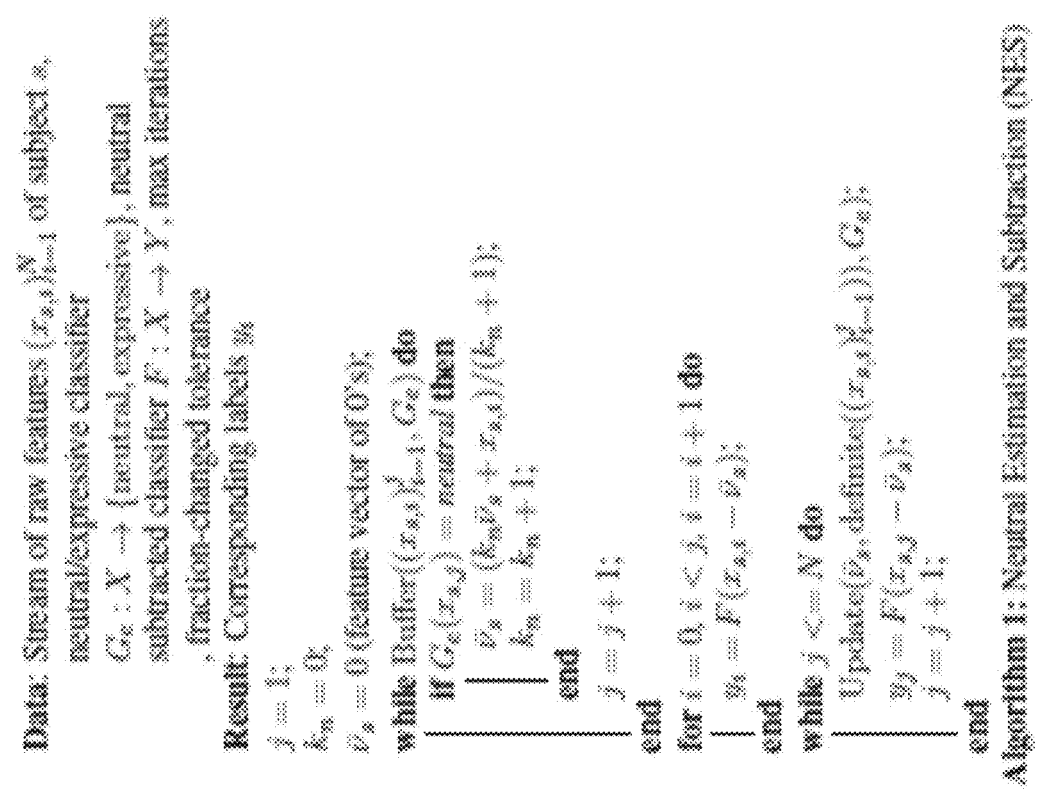

Without probabilistic outputs, many embodiments still have a number of update choices. For example, $x_{s,j}$'s update to $\bar{v}_s$ could depend on its distance from the current estimate: many embodiments could reduce its contribution to the estimate relative to Equation (5), useful if worried about outliers (if, for instance, the face tracker is unreliable). Or, in many embodiments, if it is expected that $v_s$ will change at runtime—for instance, if lighting is expected to change significantly—many embodiments can have it update the estimate of $v_s$ faster relative to Equation (5). More generally, many embodiments can allow for a definite number of statistics to be collected from all frames seen thus far $(x_{s,i})_{i=1}^{j}$, including the decisions of $G_e$, and apply a filter to estimate $v_s$. In FIG. 19, the choice of update done is referred to as Update($\bar{v}_s$,definite(($x_{s,i})_{i=1}^{j}$)),$G_e$), where "definite" refers to a restriction to a definite number of statistics collected from the stream of features (for memory purposes, many embodiments do not want to cache them all).

A low-pass filter such as an exponential moving average may provide a simple medium between being able to adapt to a changing $v_s$ and accounting for noise. The modification to Equation (5) can be simple: instead of weighting all examples classified as neutral by $G_e$ equally, many embodiments may weight the most recent ones the most, with an exponential drop-off in weight.

$$\bar{v}_s \leftarrow \alpha x_{s,j} + (1-\alpha)\bar{v}_s, 0<\alpha<1 \quad (6)$$

While a Kalman filter may prove more robust, its updates may be computationally expensive for large state dimensions, which many embodiments of the process may need to work with.

In many embodiments, the exponential moving average both guards against noise and adapts quickly to a changing $v_s$, which can be expected when lighting changes (despite lighting normalization techniques meant to mitigate this), or more drastically, when one user "hands off" the classifier to another user. Due to a lack of databases which have appropriate changes in lighting (such as a light being turned on in a room; many embodiments require more consistent changes in lighting than can be found in the Multi-Pie database).

After the update of the estimate $\bar{v}_s$, many embodiments make the predication $F(x_{s,j}-\bar{v}_s)$. The algorithm is referred to as the Neutral Estimation and Subtraction (NES) algorithm. Although the above describes a particular process for performing neutral estimation and subtraction, any of a variety of mechanisms may be utilized for performing neutral estimation and subtraction as appropriate to the requirements of specific applications in accordance with many embodiments of the invention.

Device Calibration

Affective computing that models and recognizes features of natural social conversations requires natural social interaction data. In particular, the only way to truly model natural social conversation is to learn from natural social interaction data. However, this carries with it severe labeling difficulties. In particular, labeling data for something as simple as so-called universal expressions (e.g., happy, sad, angry, surprised, fear, and disgust) in a temporally-sensitive and accurate manner is very labor intensive. Accordingly, many embodiments utilize unsupervised and active learning pre-annotation techniques that greatly cheapen the process of labeling.

In short, unsupervised techniques and noisy predictions can be used to query human experts, asking them to label a small fraction of the data and inferring labels about the rest of the data through the data's shape. For this, many embodiments adapt a variety of general active learning techniques along with systems that have found success in grammatical annotation of text. First, many embodiments gather unstructured conversational video data in laboratory sessions with typically developing participants and refine this pre-annotation scheme in the lab with expert labelers. After refining this pre-annotation scheme in the lab with expert labelers, many embodiments deploy it to users (n=100) of the therapeutic system, querying users to help better label their own data, effectively crowd-sourcing the labeling of data through human-in-the-loop learning.

Personalized Expression Recognition

Dovetailing with the above efforts, many embodiments provide domain adaptation techniques in order to tailor expression recognition systems to particular users. Domain adaptation is a machine learning task that attempts to perform well on data drawn from some target distribution for which there is little labeled or unlabeled data, given that there is more plentiful data drawn from one or many related but distinct source distributions. In particular, the task of performing well on natural social interaction data on some target set of individuals (the family for which the therapy is tailored), with most of the data consisting of other individuals, often captured in artificial laboratory, posed settings. While a general model may perform well on most individuals, there is considerable variation in accuracy across subjects, owing to natural variation in expression across people. In a therapeutic context, a recognition system that performs poorly on individuals relevant to the therapy represents a failed effort. Hence, the development of personalized expression recognition may be imperative. This may be achieved through a combination of unsupervised online and supervised domain adaptation.

In unsupervised online domain adaptation, unlabeled data is provided for the target distribution and adapted without retraining a model on all data, and a variety of techniques (e.g., online_cascade, online_multi_object, among various others) exist for making use of this. This may be thought of as a passive calibration event: the system may take in data on the subject in view and adapts the model in real time. Many embodiments of the system employ an ad hoc version of this (e.g., neutral subtraction), constructing an estimate of the current user's neutral (non-expressive) face and subtracting it away from the current face. Many embodiments of the system optimize this process, employing methods such as hier_bayes in order to discover approximately optimal adaptation.

In supervised domain adaptation, many embodiments of the system may gather labeled data on target individuals and adapt the general model to perform better on them, allowing for a more thorough retraining (not necessarily real-time). This can happen in two forms: querying users of the system to act out expressions, and asking them to confirm/correct labels on natural social interaction data gathered on them. Both of these, to varying degrees, face the potentially serious issue of vibrational scarcity, where the data gathered on the user might, aside from being scarce, not have certain kinds of important variation built in. Many embodiment of the system may thus adapt to user data while not harming the robustness the general model has to this variation.

Many embodiments of the system use hierarchical Bayesian techniques (e.g., hier_bayes) to adapt the models, allowing for fairly rapid and computationally inexpensive adaptation in both the unsupervised online and supervised contexts. This may be done in two stages. In the first stage, the system may take the naturalistic video data gathered in the above sub-aim and cross-validate in a leave-one-subject-out fashion: with source data as the aforementioned academic datasets combined with all other subjects and target training data some small subset of the target subject data, the system may validate the model on the rest of the target's natural social interaction data, labeled through the results of the above aim. In the second stage, the system may deploy the therapeutic system to participants (n=100), labeling data through the two paradigms discussed above. Although the above describes using a hierarchical Bayesian technique to adapt models, any of a variety of techniques may be utilized as appropriate to the requirements of specific applications in accordance with many embodiments of the invention.

Convolutional and Recurrent Neural Networks

Convolutional neural networks have proved particularly strong in image recognition tasks, whereas certain recurrent neural network architectures are proving useful in dealing with sequential data (e.g., captioning, handwriting). Many embodiments apply these techniques for time-dependent video expression recognition tasks. In particular, it is believed that network depth is particularly amenable to domain adaptation, and the hierarchical Bayesian methods discussed above can prove particularly fruitful for this class of learners. Many embodiments of the system apply this as primary model architecture for the domain adaptation development discussed above, with linear classifiers run on HOG features as a baseline.

Experimental Results from Various Studies

Several studies have been conducted on various aspects of the behavioral system. For example, a Google Glass prototype has been constructed that automatically tracks expressive events in faces using the Glass' outward-facing camera and a machine learning system trained on over 800,000 samples of expression data that detects 8 emotions with high accuracy (~90%). The prototype model was designed to compute on action units that stem from facial muscle movements associated with emotional expressions and to work in real time across a wide variation of faces, head position/pose, and light conditions. It was then tested on 20 autism and 20 control participants. Following consent and phenotyping using a standard autism battery (e.g., SRS), each of the 40 participants (average age of 6) was fitted with the Autism Glasses and the head-mounted pupil tracker while sitting in front of a computer screen. The screen displayed three batches of faces balanced for facial variation (e.g. race/ethnicity) for 6 seconds alongside two alternating social and non-social standardized "distractor" images from the "High Autism Interest" database. Subjects attempted to identify the emotion of faces on the screen without emotion feedback (Batch 1), with feedback provided via the "heads up" display of the Glass unit (Batch 2), and again without feedback (Batch 3). Results showed that children adapted quickly to wearing the device (several called it a "super power") and yielded preliminary data needed to tune the feedback interface; lower functioning and younger participants preferred audio to visual social feedback, compelling the build of a new software to switch the modes. All participants with autism exhibited lower baseline scores in the expression classification task than neurotypical children. However, they showed significant improvements in scores by batch 3 and within approx. 15 minutes, with scores reaching the same level as those presented by the neurotypical controls (in submission). Analysis of the eye tracking data collected in this study agreed with the finding that children with autism focus their gaze on the mouth as opposed to the eyes when looking at faces, in part explaining misclassifications of emotion prior to Glass feedback. This data support the hypothesis that even limited use can yield measurable gains and motivated the plan to advance the technology to a state of for use at home and outside of clinical laboratory environments.

Figure 21:
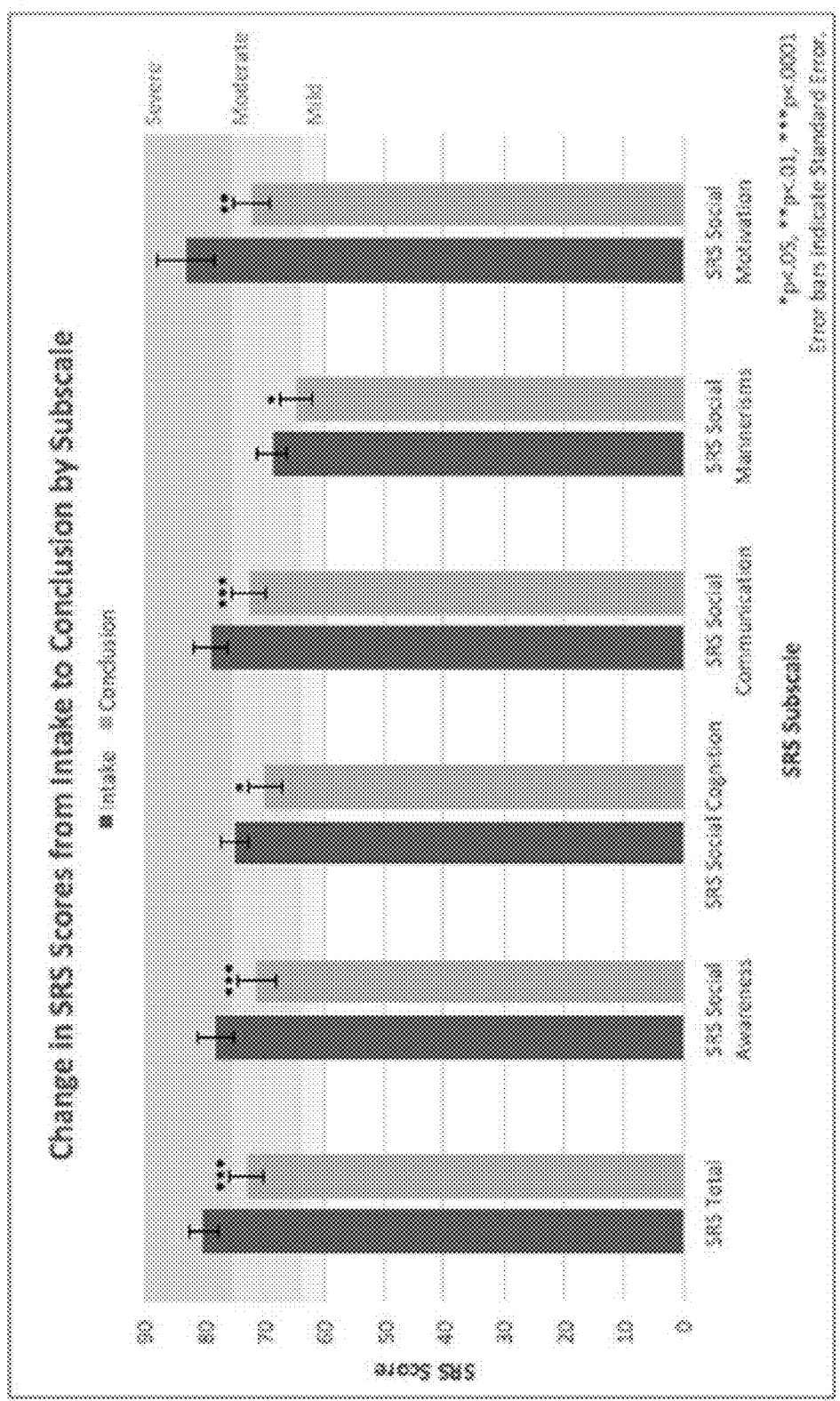
FIG. 21 illustrates a graph for a particular study showing change in SRS scores from intake to conclusion.

In another study, an embodiment of the Autism Glass was sent home with 14 families (mean age=9.57 years, SD=3.37; n=3 females) and changes were assessed from intake to conclusion (after several months using Glass) through evaluations and parental observations, mainly by the Social Responsiveness Scale second edition (SRS-2), an "emotion guessing game" (EGG) to assess how well children correctly labeled emotions in person (out of 40 questions), and parent qualitative reports. Repeated measures were used for one-way ANOVA to analyze changes in both SRS-2 and EGG scores. Participants were also asked to provide feedback on the mobile app interface. The following results were achieved, as illustrated in FIG. 20 and FIG. 21. There was a significant decrease over time in SRS-2 total scores by an average of 7.14 points ($F(1,13)=33.20$, $p=<0.001$, higher scores indicate higher ASD severity). EGG scores also significantly increased by an average of 9.55 correct responses over time ($F(1,10)=11.89$, $p=<0.01$). Over 5000 minutes of video data was recorded and analyzed. Parents reported increases in eye contact and greater social acuity. In addition, participants shared innovative feedback which led to user experience design changes on the mobile app.

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. Further, each system component and/or method step presented should be considered a "means for" or "step for" performing the function described for said system component and/or method step. As such, any claim language directed to a "means for" or "step for" performing a recited function refers to the system component and/or method step in the specification that performs the recited function, as well as equivalents thereof.

What is claimed is:

1. An image processing system, comprising:
    at least one camera for capturing images of a surrounding environment;
    at least one processor and memory containing software;
    wherein the software directs the at least one processor to:
        obtain data comprising a sequence of images captured by the at least one camera;
        detect a face for at least one person within at least one image in the sequence of images;
        detect at least one emotion in the face based upon the at least one image using a facial expression recognition module; and
        display at least one emotion indicator label corresponding to said at least one emotion to provide therapeutic feedback to a user;
    wherein the facial expression recognition module is calibrated for a target individual based on at least one image of an emotion of the target individual comprising a non-neutral facial expression to obtain improved accuracy with respect to the target individual.

2. The image processing system of claim 1, wherein the system comprises a wearable video capture system comprising at least one outward facing camera.

3. The image processing system of claim 2, wherein the wearable video capture system is selected from the group consisting of a virtual reality headset, a mixed-reality headset, an augmented reality headset, and glasses comprising a heads-up display.

4. The image processing system of claim 2, wherein the wearable video capture system communicates with at least one mobile device, wherein the at least one processor is executing on the at least one mobile device.

5. The image processing system of claim 1, wherein the software directs the at least one processor to obtain supplementary data comprising data captured from at least one sensor selected from the group consisting of a microphone, an accelerometer, a gyroscope, an eye tracking sensor, a head-tracking sensor, a body temperature sensor, a heart rate sensor, a blood pressure sensor, and a skin conductivity sensor.

6. The image processing system of claim 1, wherein display at least one emotion indicator label corresponding to said at least one emotion to provide therapeutic feedback comprises performing at least one of displaying a label within a heads-up display, generating an audible signal, generating a vibration, displaying a holographic overlay, or displaying an image.

7. The image processing system of claim 1, wherein the software directs the at least one processor to process image data at a higher resolution within a region of interest related to a detected face within an image.

8. The image processing system of claim 1, wherein the at least one emotion is detected based on at least one emotional cue detected within the at least one image, wherein the at least one emotional cue comprises information selected from the group consisting of facial expressions, facial muscle movements, body language, gestures, body pose, eye contact events, head pose, features of a conversation, fidgeting, and anxiety information.

9. The image processing system of claim 1, wherein the facial expression recognition module comprises a classifier trained using a training data set of statistically representative social expression data and that provides event-based social cues.

10. The image processing system of claim 9, wherein the classifier is a regression machine that provides continuous social cues.

11. The image processing system of claim 9, wherein the classifier is trained as visual time-dependent classifiers using video data of standard facial expressions and with expressive talking sequences.

12. The image processing system of claim 1, wherein the software directs the at least one processor to:
    prompt a user to label data for the target individual with at least one emotional cue label; and
    store the user-labeled data for the target individual in memory.

13. The image processing system of claim 1, wherein the software directs the at least one processor to store social interaction data and provide a user interface for review of the social interaction data.

14. The image processing system of claim 1, wherein the software directs the at least one processor to detect gaze events using at least one inward-facing eye tracking data in conjunction with outward-facing video data.

15. The image processing system of claim 1, wherein the software directs the at least one processor to provide a review of activities recorded and provide user behavioral data generated as a reaction to the recorded activities.

16. The image processing system of claim 1, wherein the system comprises a smart phone, desktop computer, laptop computer, or tablet computer.

17. The image processing system of claim 1, wherein the software further directs the at least one processor to calibrate the facial expression recognition module by using the at least one image of the emotion of the target individual as a baseline for the target individual to reduce an effect of physical characteristics of the target individual and lighting conditions of the at least one image in the sequence of images captured by the camera.

18. The image processing system of claim 1, wherein the user has autism.

19. The image processing system of claim 1, wherein the software further directs the at least one processor to:
    display, for each of several images previously stored within the memory of the system, an image of a face of person expressing a particular emotion, where the image is associated with the particular emotion;

receive an input from the user viewing the image regarding an emotion that the user has indicated as illustrating the emotion being portrayed by the face of the person;
determine whether the received input from the user matches the particular emotion associated with the particular image; and
provide feedback to the user based on their selection.

* * * * *